(12) United States Patent
Fordyce et al.

(10) Patent No.: US 12,227,741 B2
(45) Date of Patent: Feb. 18, 2025

(54) METHOD TO PERFORM HIGH-THROUGHPUT SINGLE CELL GENOMIC AND PHENOTYPIC ANALYSES

(71) Applicants: CZ Biohub SF LLC, San Francisco, CA (US); The Board of Trustees of the Leland Stanford Junior University, Stanford, CA (US)

(72) Inventors: Polly Fordyce, Menlo Park, CA (US); Kara Brower, Palo Alto, CA (US); Sandy Klemm, Palo Alto, CA (US); William Greenleaf, Menlo Park, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 712 days.

(21) Appl. No.: 17/257,509

(22) PCT Filed: Jul. 1, 2019

(86) PCT No.: PCT/US2019/040139
§ 371 (c)(1),
(2) Date: Dec. 31, 2020

(87) PCT Pub. No.: WO2020/009998
PCT Pub. Date: Jan. 9, 2020

(65) Prior Publication Data
US 2021/0261953 A1 Aug. 26, 2021

Related U.S. Application Data

(60) Provisional application No. 62/693,800, filed on Jul. 3, 2018.

(51) Int. Cl.
*C12N 15/10* (2006.01)
*C12Q 1/6806* (2018.01)

(52) U.S. Cl.
CPC ..... *C12N 15/1093* (2013.01); *C12N 15/1075* (2013.01); *C12Q 1/6806* (2013.01)

(58) Field of Classification Search
CPC ............ C12N 15/1093; C12N 15/1075; C12Q 1/6806
(Continued)

(56) References Cited

U.S. PATENT DOCUMENTS 7,776,927 B2   8/2010 Chu et al.
2009/0131543 A1   5/2009 Weitz et al.
(Continued)

FOREIGN PATENT DOCUMENTS

WO   2010104604 A1   9/2010
WO   2016040476 A1   3/2016
(Continued)

OTHER PUBLICATIONS

Rotem et al. High-throughput single-cell labeling (Hi-SCL) for RNA-Seq using drop-based microfluidics. PLoS ONE. 10(5), 2015, p. 1-14. [online], [retrieved on Sep. 1, 2024]. Retrieved from the Internet: <URL:https://journals.plos.org/plosone/article?id=10.1371/journal.pone.0116328> (Year: 2015).*
(Continued)

*Primary Examiner* — Aaron A Priest
*Assistant Examiner* — Randi Lynn Beil
(74) *Attorney, Agent, or Firm* — Kilpatrick Townsend & Stockton LLP

(57) ABSTRACT

The invention provides methods of performing multi-parameter analysis of single cells. Specifically, the present invention is based, in part, on leveraging a separation of reaction volume scales to conduct high-throughput single cell multi-
(Continued)

parameter measurements and library preparation on the same single cell using double emulsion micro-droplets and sorting using flow cytometry.

20 Claims, 13 Drawing Sheets

(58) Field of Classification Search
USPC .................................................. 506/26
See application file for complete search history.

(56) References Cited

U.S. PATENT DOCUMENTS

| | | |
|---|---|---|
| 2014/0220350 A1 | 8/2014 | Kim et al. |
| 2015/0376609 A1 | 12/2015 | Hindson et al. |
| 2016/0314242 A1 | 10/2016 | Schnall-Levin et al. |
| 2017/0009274 A1 | 1/2017 | Abate et al. |
| 2017/0022538 A1 | 1/2017 | Abate et al. |
| 2018/0030515 A1 | 2/2018 | Regev et al. |

FOREIGN PATENT DOCUMENTS

| | | |
|---|---|---|
| WO | 2017066231 A1 | 4/2017 |
| WO | 2017070056 A1 | 4/2017 |
| WO | 2017075297 A1 | 5/2017 |
| WO | 2017165791 A1 | 9/2017 |
| WO | 2017197338 A1 | 11/2017 |

OTHER PUBLICATIONS

Mazutis et al. Single-cell analysis and sorting using droplet-based microfluidics. Nat Protoc. 8(5), 2013, 870-891. (Year: 2013).*
Hosokawa et al., "Massively Parallel Whole Genome Amplification for Single Cell Sequencing Using Droplet Microfluidics", Scientific Reports, Jul. 12, 2017, pp. 1-11, , vol. 7, Issue 1.
Kim et al., "Single-Cell RT-PCR in Microfluidic Droplets with Integrated Chemical lysis", Anal Chem., Dec. 19, 2017, pp. 1273-1279, vol. 90, Issue 2.
PCT/US2019/040139, "International Search Report and Written Opinion", Oct. 22, 2019, 12 pages.
Terekhov et al., "Microfluidic Droplet Platform For Ultrahigh-Throughput Single-Cell Screening Of Biodiversity", Proc Natl Acad Sci,, Mar. 7, 2017, pp. 2550-2555, vol. 114, Issue 10.
Zinchenko et al., "One in a Million: Flow Cytometric Sorting of Single Cell-Lysate Assays in Monodisperse Picolitre Double Emulsion Droplets for Directed Evolution", Analytical Chemistry, Feb. 11, 2014, pp. 2526-2533, vol. 86, Issue 5.
Bernath et al. "In vitro compartmentalization by double emulsions: sorting and gene enrichment by fluorescence activated cell sorting." Analytical biochemistry 325.1 (2004): 151-157.
Lim et al., "Ultrahigh-throughput sorting of microfluidic drops with flow cytometry." Lab on a chip13.23 (2013): 4563-4572.
Sukovich et al., "Sequence specific sorting of DNA molecules with FACS using 3dPCR." Scientific reports 7 (2017): 39385.
Macosko et al. "Highly parallel genome-wide expression profiling of individual cells using nanoliter droplets." Cell 161.5 (2015): 1202-1214.
Klein et al. "Droplet barcoding for single-cell transcriptomics applied to embryonic stem cells." Cell 161.5 (2015): 1187-1201.

* cited by examiner

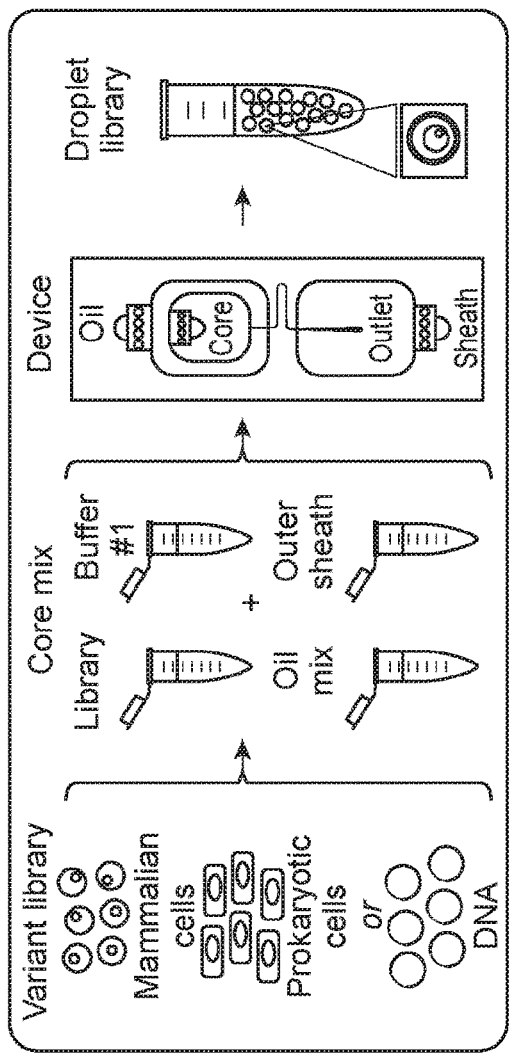
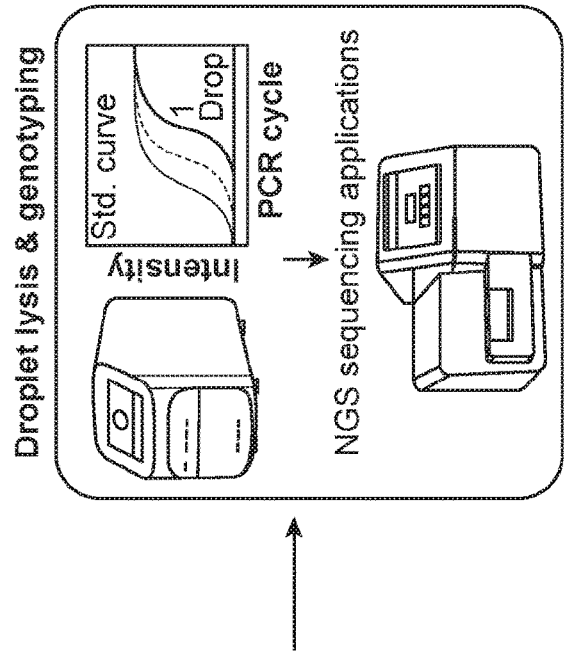
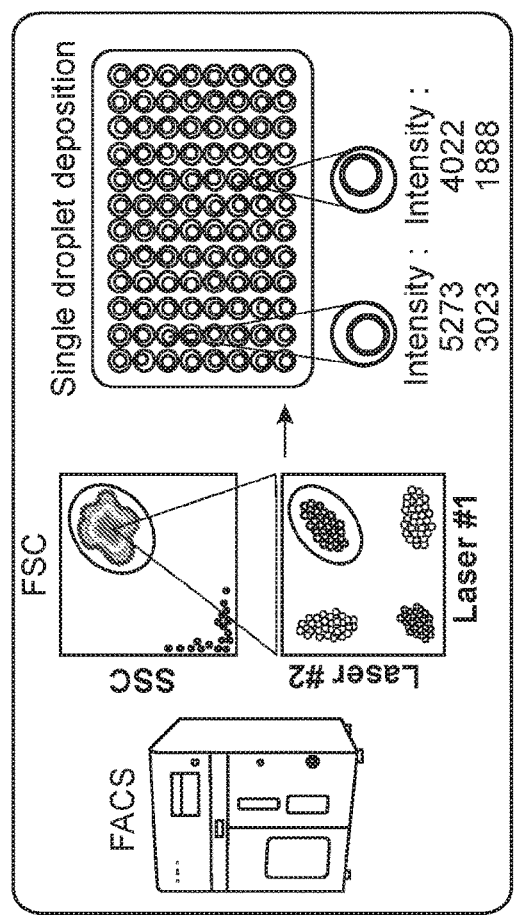
FIG. 1A
FIG. 1C
FIG. 1B

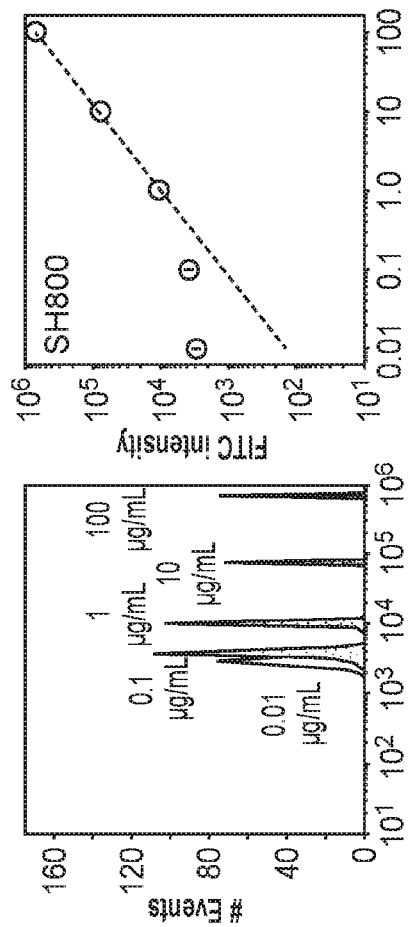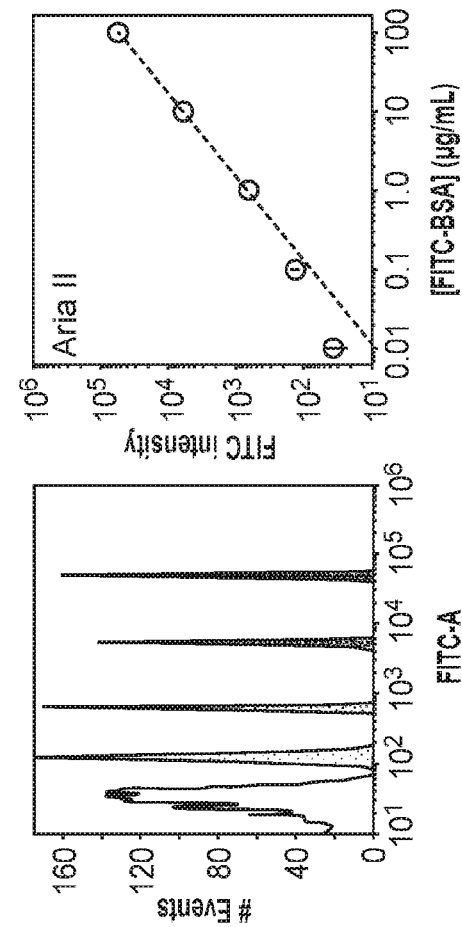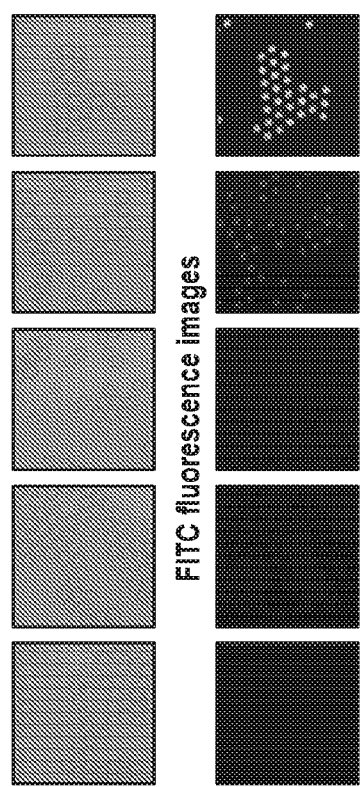
FIG. 6A
FIG. 6B
FIG. 6C

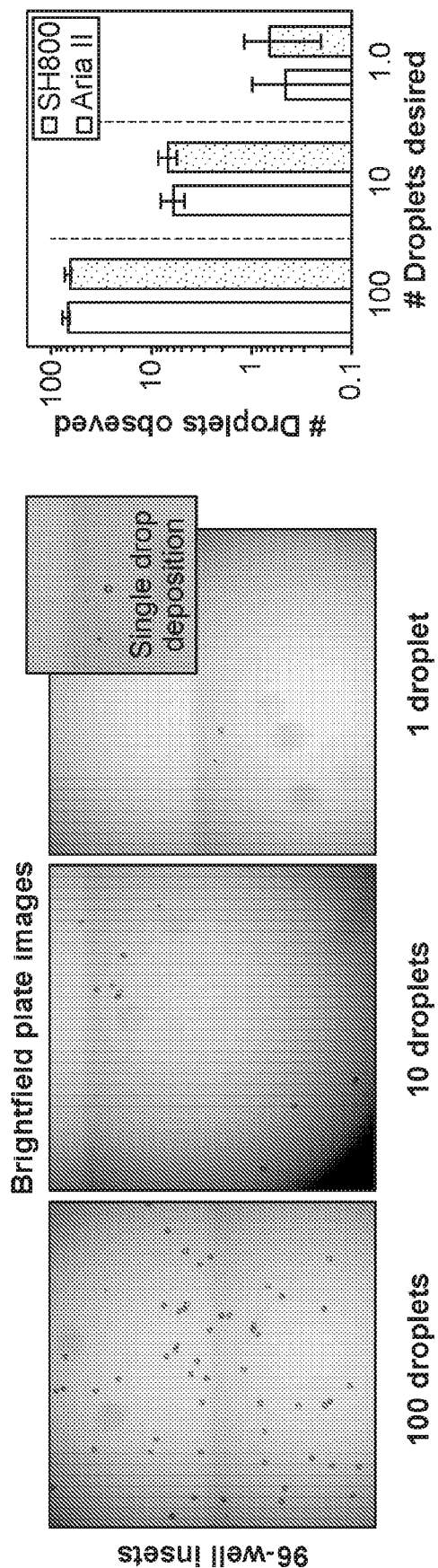

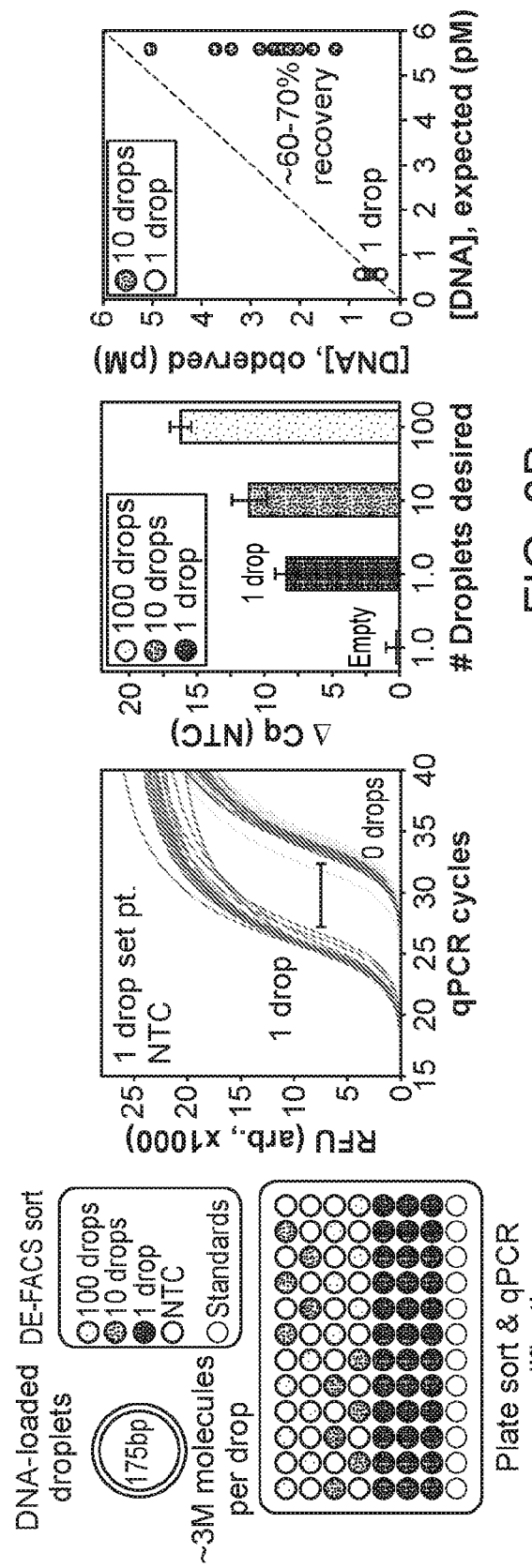
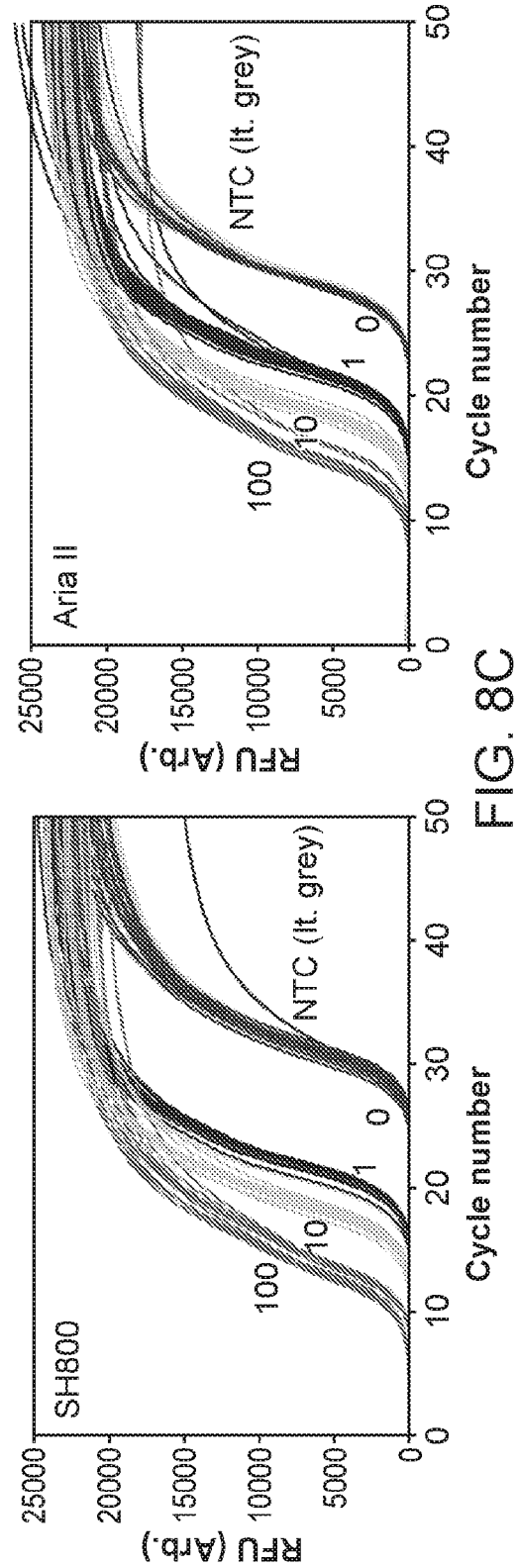
FIG. 8A
FIG. 8B
FIG. 8C

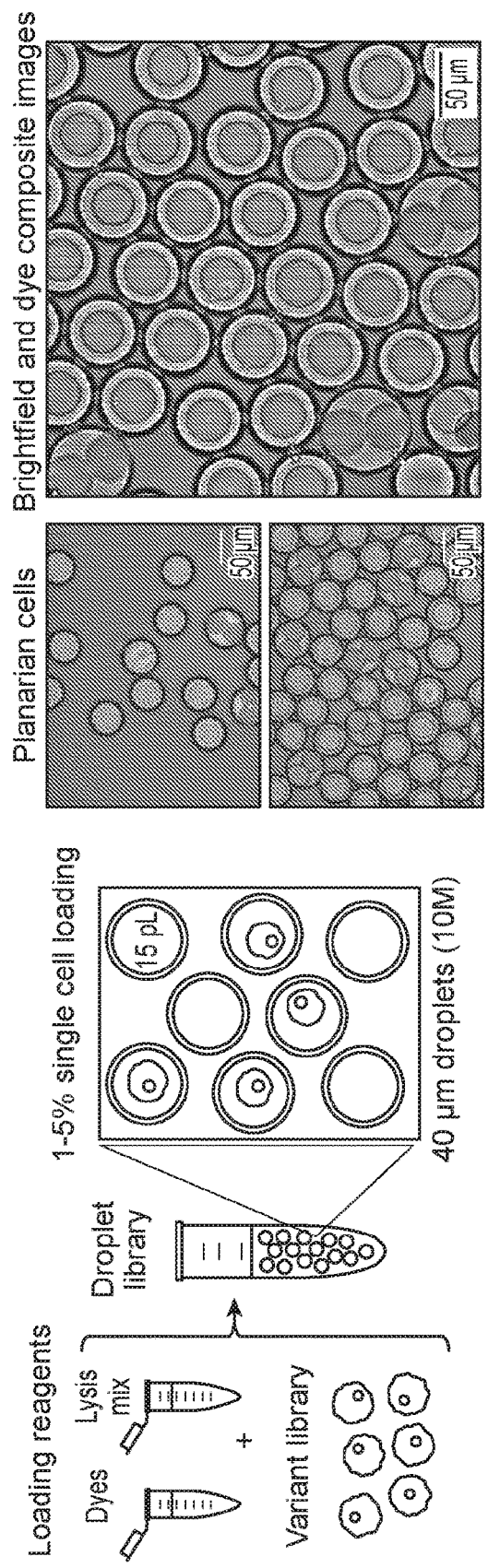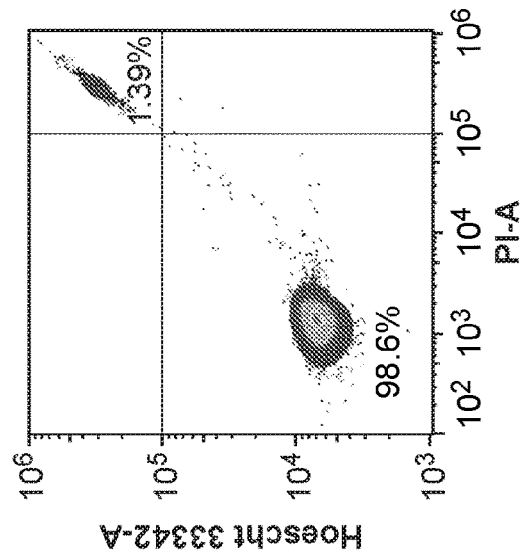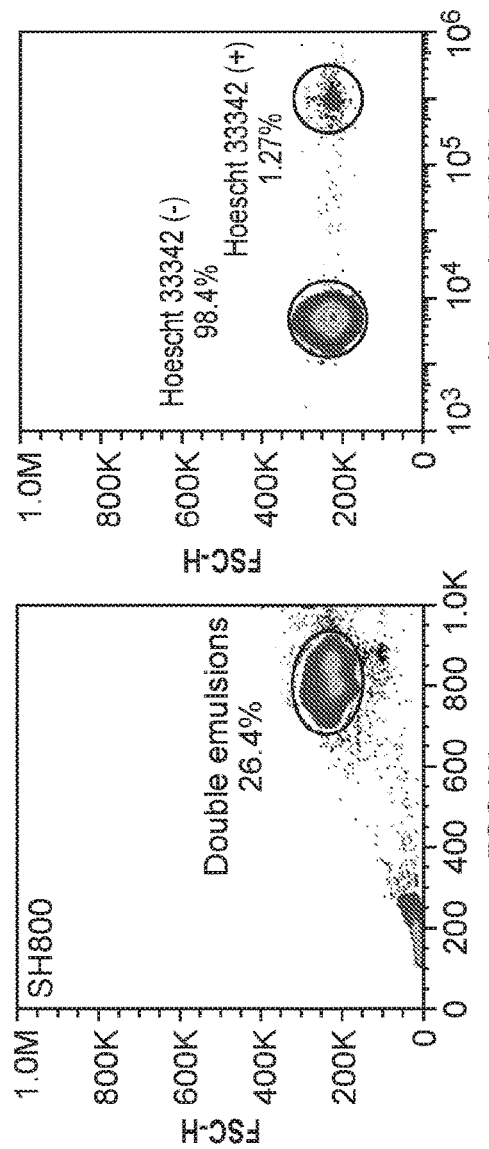
FIG. 9A
FIG. 9B
FIG. 9C
FIG. 9D
FIG. 9E

METHOD TO PERFORM HIGH-THROUGHPUT SINGLE CELL GENOMIC AND PHENOTYPIC ANALYSES

CROSS-REFERENCE TO RELATED APPLICATIONS

This application is a National Stage application of PCT Application No. PCT/US2019/040139, filed Jul. 1, 2019, which claims priority to U.S. provisional application No. 62/693,800, filed Jul. 3, 2018, which is incorporated by reference herein.

BACKGROUND OF THE INVENTION

Methods to quantify or assess differential expression and organization of biomolecules (e.g., genomic DNA, chromatin structure and accessibility, and RNA and protein expression,) in single cells are important in understanding complex biological phenotypes. A variety of single-cell methods have been described to analyze expression and or other characteristics of a single class of biomolecules; however, multi-parameters molecular measurements on the same single cell are throughput-limited and often require laborious, physical separation of the contents of a single cell.

BRIEF SUMMARY OF CERTAIN ASPECTS OF THE INVENTION

The present invention is based, in part, on leveraging a separation of reaction volume scales to conduct high-throughput single cell multi-parameter measurements and library preparation on the same single cell using double emulsion micro-droplets and sorting using flow cytometry. Methods as described herein employ the throughput and precision of single cell droplet encapsulation and flow cytometry-based single droplet-deposition sorting to provide the ability to perform a single-class measurement inside the droplet volume, sort the population of droplets by cellular presence or reaction completion to identify droplets that contain single cells and distribute these individually to higher volume compartments, thus allowing multi-parameter analysis of a single cell.

Thus, in the present disclosure, multi-parameter measurements are performed for the same single cell in which a first assay to assess a parameter is performed in a droplet volume of a double-emulsion droplet, the population of droplets is sorted to identify single droplets that contain cells, or the contents of the cells, and the single droplets are deposited into higher volume compartments for dilution and measurement of one or more additional parameters.

In one aspect, the disclosure provides a method of producing a library of cells for multi-parameter analysis, wherein the method comprises: (a) generating a population of double emulsion droplets at least some of which comprise single cells encapsulated therein, wherein the double emulsion droplets further comprise reagents for a first single cell assay to analyze a first parameter; (b) incubating the droplets for a time sufficient to generate a reaction product for the first single cell assay; (c) sorting the population of droplets by flow cytometry to select for single droplets, and optionally selecting for droplets in which a reaction occurred and distributing single droplets into separate wells; (d) breaking individual droplets in each well to produce a plurality of individual wells each containing the content of an individual droplet; (e) diluting the contents of the individual wells by at least 100-fold, e.g., a 1,000-fold to 100,000-fold, to provide a diluted reaction volume; and (f) measuring a second parameter in a second single cell assay in the diluted volume. In some embodiments, the method further comprises a Step of processing the contents of the diluted reaction volume for analysis of the reaction product for the first single cell assay. The analysis of the reaction product for the first single cell assay may be used to determine the first parameter. In some embodiments, the reaction product generated in Step (b) is not detectably labeled (e.g., is not fluorescently labeled) and/or the presence, absence or amount of the reaction product generated in Step (b) is not a basis for sorting droplets in Step (c). In some embodiments, diluting Step (e) employs a diluent that comprises reagents that differ from the first single cell assay reagents. In some embodiments, the droplets of Step (a) comprise cell-lysing buffer to lyse the cells in the droplet volume. In some embodiments, Step (d) is performed by breaking dry droplets by osmotic or shear force. In some embodiments, the processing step comprises an amplification reaction to index the contents of the compartments by the addition of barcodes unique to each well; and pooling the contents of individual wells for purification, amplification, or further analysis. In particular embodiments, the pooled contents are sequenced by massively parallel sequencing. In some embodiments, the wells are components of a multi-well plate, for example, a multi-well plate that comprises 96, 384, or 1536 wells. In some embodiments, greater than 50%, greater than 70%, or greater than 80% of the wells contain single droplets containing a single cell or the content of a single cell. In some embodiments, cells encapsulated in the double emulsion droplets of Step (a) are eukaryotic cells, such as mammalian cells, e.g., human cells. In some embodiments, cells encapsulated in the double emulsion droplets of Step (a) are tumor cells, embryonic stem cells or lymphocytes. In some embodiments, Step (c) comprises FACS sorting based on DNA content of the droplet. In some embodiments, single droplets selected in Step (c) contain a haploid cell or the content of a haploid cell. Alternatively, droplets selected in Step (c) may contain a diploid cell or its contents; or a cell that has a ploidy greater than diploid or its contents. In some embodiments, cells encapsulated in the double emulsion droplets of Step (a) are labeled with a fluorescent DNA intercalating dye for sorting by flow cytometry. In some embodiments, cells encapsulated in double emulsion droplets of Step (a) are undergoing DNA replication and are labeled by incorporating a fluorescently coupled nucleoside analog for sorting by flow cytometry. In some embodiments, cells encapsulated in double emulsion droplets of Step (a) are labeled with a fluorescent assay reagent for sorting by flow cytometry. In some embodiments, cells encapsulated in double emulsion droplets of Step (a) are labeled with a fluorescent dye coupled to a protein, e.g., an antibody, for sorting by flow cytometry. In some embodiments the first single cell assay is ATAC-Seq and the second single cell assay is RNA-Seq; ChIP-Seq, whole genome sequencing, or a protein detection assay. In further embodiments, the first single cell assay is ATAC-Seq and the second single cell assay is an RNA analysis assay, e.g., RNA-Seq. In some embodiments, the first single cell assay is a protein detection assay and the second single cell assay is RNA-Seq; ChIP-Seq, ATAC-Seq, or whole genome sequencing. In some embodiments, the first assay detects expression of at least one gene of interest and the second assay is an RNA-Seq assay, for example, the first assay may comprise an RT-PCR amplification reaction to specifically detect expression of the least one gene of interest, wherein the RT-PCR reaction comprises an oligonucleotide labeled with a detectable label, and wherein the oligonucleotide specifically hybridizes to a target nucleic acid sequence in the gene of interest; and the sorting Step c) comprises selecting droplets that contain a signal from the detectable label. In some embodiments, the double emulsion droplet is about 20-30 micrometers in diameter and a flow nozzle of 100 micrometers or 130 micrometers is used for flow cytometry. In some embodiments, the double emulsion droplet is 30-50 micrometers in diameter and a flow nozzle of 100 micrometers or 130 micrometers is used for flow cytometry. In some embodiments, the double emulsion droplet is 50-125 micrometers in diameter and a flow nozzle of 130 micrometers is used for flow cytometry.

In a further aspect, the disclosure provides a method of producing a library of containing organelles from a single cell, e.g., nuclei, mitochondria, or plastids, e.g., chloroplasts, for multi-parameter analysis, in which the organelles are encapsulated in double emulsion droplets instead of cells. The droplet volume may be adjusted as appropriate for the organelle, e.g., nuclei. Thus, in some embodiments, the method comprises: (a) generating a population of double emulsion droplets at least some of which comprise organelles, e.g., nuclei, from single cells encapsulated therein, wherein the double emulsion droplets further comprise reagents for a first single cell assay to analyze a first parameter; (b) incubating the droplets for a time sufficient to generate a reaction product for the first single cell assay; (c) sorting the population of droplets by flow cytometry to select for single droplets, and optionally selecting for droplets in which a reaction occurred and distributing single droplets into separate wells; (d) breaking individual droplets in each well to produce a plurality of individual wells each containing the content of an individual droplet; (e) diluting the contents of the individual wells by at least 100-fold, e.g., a 1,000-fold to 100,000-fold, to provide a diluted reaction volume; and (f) measuring a second parameter in a second single cell assay in the diluted volume. In some embodiments, the method further comprises a step of processing the contents of the diluted reaction volume for analysis of the reaction product for the first single cell assay. In some embodiments, diluting Step (e) employs a diluent that comprises reagents that differ from the first single cell assay reagents. In some embodiments, the droplets of Step (a) comprise membrane-lysing buffer to lyse organelle membranes in the droplet volume. In some embodiments, Step (d) is performed by breaking dry droplets by osmotic or shear force. In some embodiments, the processing step comprises an amplification reaction to index the contents of the compartments by the addition of barcodes unique to each well; and pooling the contents of individual wells for further analysis. In particular embodiments, the pooled contents are sequenced by massively parallel sequencing. In some embodiments, the wells are components of a multi-well plate, for example, a multi-well plate that comprises 96, 384, or 1536 wells. In some embodiments, greater than 50%, greater than 70%, or greater than 80% of the wells contain single droplets containing an organelle, e.g., a nucleus, from a single cell. In some embodiments, organelles, e.g., nuclei, encapsulated in the double emulsion droplets of a) are from eukaryotic cells, such as mammalian cells, e.g., human cells. In some embodiments, organelles, e.g., nuclei, encapsulated in the double emulsion droplets of a) are tumor cells, embryonic stem cells or lymphocytes. In some embodiments, Step (c) comprises FACS sorting based on DNA content of the droplet. In some embodiments, single droplets selected in Step (c) contain an organelle, e.g., a nucleus, from a haploid cell. Alternatively, droplets selected in Step (c) may contain an organelle, e.g., a nucleus, from a diploid cell, or from a cell that has a ploidy greater than diploid. In some embodiments, organelles, e.g., nuclei, encapsulated in the double emulsion droplets of Step a) are labeled with a fluorescent DNA intercalating dye for sorting by flow cytometry. In some embodiments, organelle, e.g., nuclei, encapsulated in double emulsion droplets of Step (a) are from cells undergoing DNA replication and are labeled by incorporating a fluorescently coupled nucleoside analog for sorting by flow cytometry. In some embodiments, organelles, e.g., nuclei, encapsulated in double emulsion droplets of Step (a) are labeled with a fluorescent assay reagent for sorting by flow cytometry. In some embodiments, organelles, e.g., nuclei, encapsulated in double emulsion droplets of Step (a) are labeled with a fluorescent dye coupled to a protein, e.g., an antibody, for sorting by flow cytometry. In some embodiments, the first single cell assay is ATAC-Seq and the second single cell assay is RNA-Seq; ChIP-Seq, whole genome sequencing, or a protein detection assay. In further embodiments, the first single cell assay is ATAC-Seq and the second single cell assay is an RNA analysis assay, e.g., RNA-Seq. In some embodiments, the first single cell assay is a protein detection assay and the second single cell assay is RNA-Seq; ChIP-Seq, ATAC-Seq, or whole genome sequencing.

BRIEF DESCRIPTION OF THE DRAWINGS

FIG. 1A-C provide an overview of an illustrative assay of the present disclosure.

FIG. 6A-F, shows comparative flow dynamic range and sensitivity analysis of 30 um double emulsion droplets containing FITC-BSA as the fluorophore Alexa-647-BSA as the fluorophore in concentrations ranging from 0.01 ug/mL to 100 ug/mL (5 droplet populations, brightfield and fluorescent channel visualizations shown).

FIG. 7A-C, depicts 96-well plate sorting on SH800 (Sony) from a dilutional series down to single droplet resolution for single droplet deposition.

FIG. 8A-C shows nucleic acid recovery and quantitative PCR (qPCR) for a small (175 bp DNA fragment) from single droplet deposition and droplet lysis in plates.

FIG. 9A-E, show single cell loading in double emulsion droplets.

DETAILED DESCRIPTION

Figures 2A, 2B:
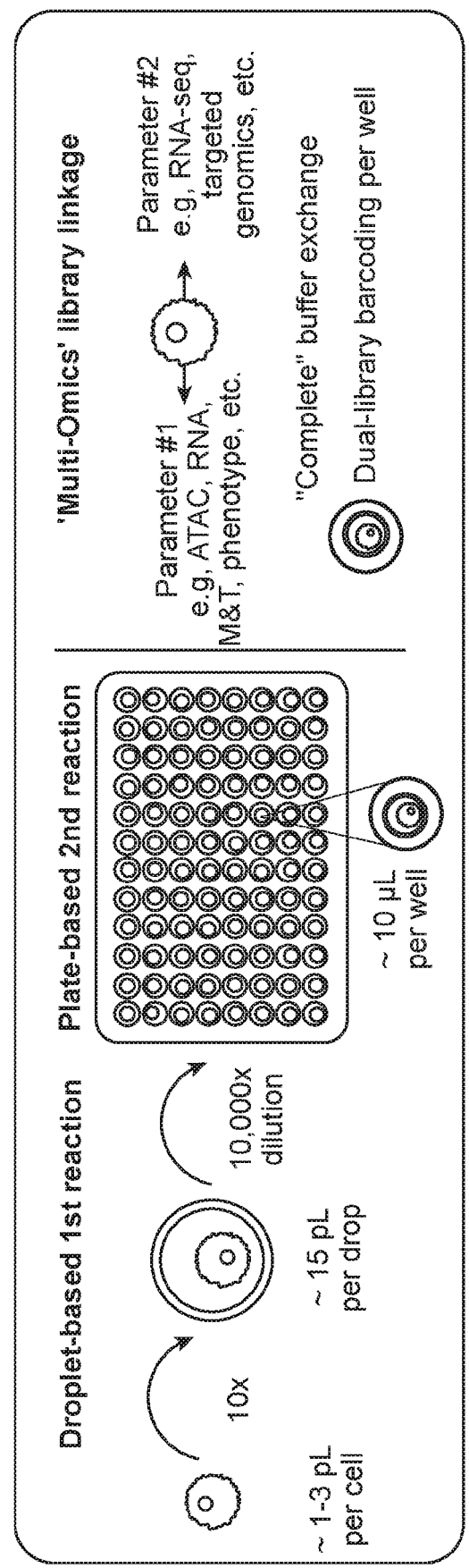
FIG. 2A-B illustrate a plate-based dilution scheme via single droplet deposition of double emulsion droplets after FACS. In the scheme shown in Panel A, the first library reaction is completed within the droplet volume (~100 pL) and a second library preparation reaction to achieve sequential multi-parameter single cell analysis is completed in the much larger plate volume (e.g. ~10-20 uL) after droplet deposition. This dilution scheme achieves 1,000-100,000-fold dilution, overcoming "one-pot" library preparation and purification issues and incompatibilities. Illustrative multi-parameter single cell analyses possible with double emulsions in the droplet to plate sorting scheme are shown in Panel B.

The present invention employs double emulsion droplets that comprise single biological entities (e.g., eukaryotic cells or organelles from single cells) and reagents for labeling cells and generating a biomolecule processed product for single cell analysis in an assay to measure a parameter of interest, e.g., genome structural analysis, RNA expression profiling, haplotype analysis and/or protein expression profiling and the like.

A "parameter," in this context, refers to a characteristic of a cell or cell component (e.g., transcriptome) of interest. A "parameter" is determined by an "assay." For illustration and not limitation, exemplary assays include binding assays, immunoassays, amplification assays, hybridization assays and the like. In an additional aspect, an assay may be a process that produces a product for further analysis to determine a parameter. For example, amplification of a target sequence may be an assay. As used herein with respect to a multi-parameter analysis, a "first" assay refers to a single cell assay performed, at least in part, in a droplet prior to droplet sorting, and may also be referred to herein as a "droplet-based assay." A "second" assay refers to a single cell assay performed in a well following dilution of the contents of a single-cell-containing droplet after the droplet has been broken open in the individual well in which it is deposited. Unless otherwise specified, "droplets" as used herein refers to double emulsion droplets.

Droplet Formation

Methods for preparing double emulsion droplets have been described (see, e.g., U.S. Patent Application Publication Nos. 20170022538, 20170121756, 2009131543, and 201422035; and International Patent Publication WO2010104604, the disclosures of which are is incorporated by reference for preparation of double emulsion droplets). Any method may be employed to produce the double emulsion droplets as described herein. In brief, droplets are typically generated using a microfluidic device in which aqueous streams are used to prepare an aqueous miscible core (sometimes, "core") comprising cells and reagents, which is then encapsulated in an immiscible oil shell (sometimes, "shell") and an outer aqueous layer. In typical embodiments, the double emulsion droplets comprise stabilizing agents, such as surfactants (see, e.g., US20170022538). Double emulsion droplets may also be prepared in which organelles from cells are encapsulated into the droplets using the methods described below.

The generated double emulsion droplets are typically 1 to 1,000 micrometers in diameter. In some embodiments, double emulsion droplets have a diameter of about 5 micrometer to 500 micrometers in diameter. In some embodiments, the droplets range in size from about 10 to 1,000 micrometers or about 10 to 500 micrometers in diameter. In some embodiments, the diameter is about 10 to about 250 micrometers. In some embodiments, the diameter is 10 to 100 micrometers e.g., about 20 to about 50 micrometers in diameter. In some embodiments, the droplets are about 30 to about 40 micrometers in diameter. The double emulsion droplets have a substantially homogenous distribution of diameters, for instance, within a population of droplets for multi-parameter evaluation, the coefficient of variation (CV), which is the mean diameter over standard deviation) is less than 10% and often less than 5%. Typically the CV is 2.5% or less. Droplet diameter can be determined using various techniques, including optical microscopy, laser light scattering or other techniques.

A double emulsion droplet as used in the present invention typically has an internal volume within the range of about 1 picoliter (pL) to about 50 nanoliter (nL) or within the range of about 100 pL to about 20 nL. for example, about 1 pL to about 1 nL, about 10 pL to about 500 pL, or from about 50 pL to about 500 pL. In some embodiments, the volume ranges in size from about 10 picoliter to about 600 pL, e.g., from 14 pL to 35 pL As used in this context, the term "about" refers to a typical standard deviation in droplet volume of a population of double emulsion droplets of the size and uniformity of diameter indicated in the preceding paragraph. In some embodiments, the droplet volume is may have an internal volume from about 0.001 pL to about 1 pL in size, or from about 0.01 to about 0.1 pL in size. Thus, in some embodiments, the double emulsion droplet may range in size from 0.001 pL to 50 nL.

Reagents that are incorporated into double emulsion droplets in accordance with the present disclosure include, for example, lysis buffers, detection agents, and reaction agents for processing biomolecules for analysis. Reaction agents include enzymes, agents that detect proteins, e.g., antibodies, and other reagents that are used for single cell analysis, such as ATAC-Seq, RNA Seq, protein detection assays, haplotype determination, and the like. In some embodiments, the droplets comprise cells and an agent to label the cell for droplet detection by flow cytometer, e.g., a DNA-intercalating dye. In some embodiments, agents incorporated into the double emulsion droplet include reagents that can be used to enrich for droplets containing cells that have a desired phenotype, e.g., an antibody, or polypeptide to detect a cell surface marker.

In some embodiments, cells in a population of cells are introduced into droplets using dilution to control distribution of cells in droplets (e.g., to maximize the proportion of droplets containing a single cell or to minimize the proportion of droplets containing multiple cells. In such embodiments, dilutions may be based on the number of cells to generate a population of droplets that reflect Poisson statistics with respect to the number of cells in a droplet. However, in some embodiments, encapsulation of a population of cells into droplets may deviate from Poisson statistics, for example, if the droplet volume excludes certain cells. Methods are known for generating a population of droplets in which a greater number of droplets, compared to a Poisson distribution, contain single cells (see, e.g., Collins et al., *Lab Chip*, 15:3439-3459, 2015 and references cited therein). In further embodiments, cells are loaded into droplets at a limiting dilution that results in a "sub-Poisson" distribution, for example, such that about 80% or greater of the droplets contain no cells to optimize for single cell-containing droplets at the exclusion of multi-cell droplets.

Cells and buffers comprising reagents for a droplet-based single cell analysis are co-encapsulated into droplets using separate aqueous streams to obtain the double emulsion droplets. A chemical lysis agent, e.g., a detergent, such as a non-ionic detergent, may be, but need not be, depending on parameter to be measured, included in the reagents to lyse a cell contained in the droplet.

Droplet-Based Assay (First Assay)

As noted above, one or more first assays are carried out in droplets. The droplets comprising biological entities (e.g., cells) may be incubated for a sufficient time e.g., from 30 sec up to several hours, e.g., up to 3, 4, 5, or 6 hours, to generate reaction products. In some embodiments, droplets are incubated for a period of time from 30 minutes up to 3 hours; or from 30 minutes up to 2 hours under conditions (e.g., temperature) suitable for assay reactions to proceed.

First assays are not limited to any particular assay or type of assay, with the provisos that first assays take place in the droplet volume and under the conditions in the droplet core volume.

Some first assays result in production of a signal detectable during the droplet sorting step. Some first assays result in production of a assay reaction product that is further processed after.

In some embodiments, barcodes may be added during a reaction performed in the droplet volume.

In some embodiments, cells may be labeled with a fluorophores, stain or dye, including intercalating dyes, for droplet sorting to identify droplets containing at least one cell based on the presence of nucleic acid. In some embodiments, DNA dyes (e.g., intercalating dyes) are used to identify droplets comprising single cells, based on nucleic acid content. In some embodiments, cells incorporated into droplets are labeled with a fluorescent dye that binds to DNA. Illustrative fluorescent dyes include that bind DNA include Hoechst, PicoGreen, DAPI, Propidium iodine, SYBR-family dyes, YOYO-1-family dyes, and others.

In some embodiments, cells encapsulated in droplets are undergoing DNA replication and are labeled by incorporating a fluorescently coupled nucleoside analog into the DNA. In some first assays a detectable signal is produced only of a specified nucleic acid sequence is present in the droplet.

In one first assay, a dead or non-viable cell is distinguished from living cell based on cell integrity or metabolic properties. See, e.g., Niles et al., *Anal Biochem.* 366:197-206, 2007.

Droplets may also be sorted based on labeling of membrane proteins or lipids, or other biomolecules of encapsulated cells for FACS analysis. In some approaches the presence of a specific protein(s), such as a transcription factor, is detected. See, e.g., Ma, J., 2018, *Anal Chim Acta.* 1029:72-77, 2018. In some embodiments a proximity extension or proximity ligation assay is used.

In some embodiments, fluorescent dyes are attached, via covalent or non-covalent interactions, to agents, e.g., antibodies, that directly or indirectly label biomolecules present on the cell surface, e.g., receptors, transporters, or other cell surface markers, or other internal biomolecules that are accessible to the labeling agent for binding when the cell is lysed. In some embodiments, products generated during the reactions for the droplet-based single cell assay, i.e., the assay for the first biomolecule parameter, may be labeled with an appropriate fluorescent dye. Illustrative fluorophores useful for labeling for FACS sorting of the population of droplets include indocarbocyanine (C3), inododicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), and carboxy-X-rhodamine (ROX).

Detectable labels other than fluorescent labels may be used in certain embodiments, if they are detectable using a cell sorting (CS) device. For example, luminescence, chemiluminescence and bioluminescence labels may be used.

In certain embodiments, a first assay results in production of an assay reaction product that is further processed after breaking the droplet and diluting the droplet core. The terms "processed," "processing" and the like, in this context, refer to additional manipulation of the reaction products to prepare an end-product to be measured, detected, or analyzed. For illustration, a first assay reaction product can be amplicons generated in a droplet, and processing can include preparing an indexed sequencing library from the amplicons, e.g., by amplifying and adding barcodes to the amplicons. In certain embodiments, more than one (e.g., two or three) first assays result in production of assay reaction products that are further processed.

In some embodiments, in addition to first and second assays, cells may be labeled prior to encapsulation into droplets.

Droplet Sorting and Large-Volume Analysis

The double emulsion droplets are analyzed and gated based on the fluorescent dye or dyes used as the cell-labelling agent, e.g., DNA-intercalating dye, to identify single droplets at least some of which contain single cells. Sorted single droplets are deposited into individual wells, e.g., wells in a multi-well plate, that accommodate a volume much greater than that of a single droplet. Although at least some portion of single droplets selected by sorting will contain a single cell, or the contents of single cell, some of the selected droplets may contain more than one cell. Thus, for example, an individual selected single droplet may contain two or three cells (or the contents of the cells). In some embodiments, sorting provides a population of single droplet-containing wells in which the proportion of droplets containing single cells, or the contents thereof, is at least 50%, e.g., 70% or greater. Various multi-well plate formats are available. common multi-well plates include 96-well, 384-well, and 1536-well plates. Although the term "well" is used throughout the disclosure, any compartment, e.g., tubes, suitable for depositing cells into which a diluent can be added to substantially dilute the droplet contents, e.g., by at least 100-fold, for example about 1,000-fold to about 100,000-fold, as described herein, may be used.

Single droplets are broken in the individual wells in which they are deposited, resulting in a well containing the contents of the droplet. Cells may be broken by any method, including chemical, electrical, or mechanical methods such as sonication. In some embodiments, droplets are broken by osmotic or shear force. In an exemplary embodiment, droplets are broken by osmotic force, i.e., droplets are "popped" on dry plates. Droplets are "popped" by sorting droplets into dry wells and allowing the droplets to sit for a period of time, for example, from 30 sec to 90 sec, e.g., 60 secs, sufficient for the droplet to break. Various other methods for breaking droplets are described, e.g., in De Lange et al, *Biomicrofluidics* 10(2):024114, 2016.

The contents from the broken droplets are diluted in the well for measuring additional parameters of interest. The droplet contents can be diluted to a volume that is much greater than that of the initial droplet, thus allowing for assaying a second parameter even if there are components from the first assay (conducted in the droplet volume) that may not be compatible with the second assay. In specific embodiments a reagent, product, buffer, pH, from a first assay is not compatible with the second assay. In this context, "not compatible" means the second assay cannot be carried out under the conditions of the first assay or, can be carried out but results in a suboptimal result.

Dilution is typically at least 100-fold. In some embodiments, the contents of an individual droplet are diluted up to 100,000-fold, up to 200,000-fold, or up to 500,000-fold. In some embodiments, the contents are diluted in a range of 100-fold to 200,000-fold; or 1,000 to 100,000-fold. In some embodiments, the contents are diluted from 10,000-fold to 100,000-fold. For example, a droplet volume of 100 picoliter may be diluted to 10 to 20 microliters following distribution of sorted single droplets into separate compartments.

Following deposit into a well and dilution, one or more assays in addition to the droplet-based assay can be performed to measure additional parameters.

In some embodiments, products generated in the droplet-based assay ("first assay products") are processed after dilution to produce a signal, assayable product (e.g., a nucleic acid library), or a substrate for a third assay. In some embodiments the first assay products are processed in wells, for example, using one or more amplification reactions, such as an amplification reaction comprising PCR, to obtain a final product for analysis, e.g., by massively parallel sequencing. In some embodiments, at least some first assay products are not detected and/or produce no detectable signal during the droplet stage.

In some assays, sequencing barcodes (or indexes) are added to the plate and the initial library is amplified and pooled for processing. In other assays, sequencing barcodes and reagents for dual-library processing are added to the plate and multiple single cell analysis libraries are processed at once by plate-based dilution for the second assay. This approach takes advantage of existing plate-based processing methods for performing a dual-library preparation. In some assays, droplets could be recovered instead of processed if desired. Resultant libraries are pooled and sequenced together for single or dual parameter next generation sequencing analyses from the same single cell.

"Massively parallel sequencing" has its normal meaning in the art, and refers to high throughput DNA sequencing methods that employ specific 'index' or sample tracking and hybridization sequences that are compatible with the particular massively parallel sequencing technology. Sequencing libraries can be prepared from cellular DNA or RNA after processing and amplification steps. In some embodiments, a unique barcode identifier may be employed to identify the contents of an individual well, so that a library can be generated by pooling the contents of multiple wells. Resultant libraries may be sequenced together for single or dual parameter sequencing analyses of the same single droplet. In some assays, if desired, droplets may be recovered instead of processed. Methods of indexing samples using barcodes are known, see, e.g., US Patent Application Publication Nos. 20150298091, 20150376609, 20160314242 and 20180030515 and references cited in the following section.

Single-Cell Assays

Various single cell assays can be used in multi-parameter single cell analysis in accordance with the invention. Exemplary assays include ATAC-Seq, ChIP-Seq, genomic DNA sequencing, including haplotyping and phase determination, methylation profiling, RNA sequencing, and protein marker detection. Such assays can be performed in the droplet prior to sorting or as a second assay following dilution of the contents of the single droplets.

In some embodiments, one parameter assayed in accordance with the present invention is chromatin accessibility as determined using a single cell ATAC-Seq assay (see, e.g., Buenrostro et al., *Nat. Methods* 10: 1213-8; 2013; Cusanovich, et al., *Science* 348:910-4. 2015; Qu et al., *Cell Systems* 1:51-61, 2015; Chen et al., *Nat. Methods* 13:1013-1020, 2016). In some embodiments, ATAC-Seq is performed in the double emulsion droplets. In alternative embodiments, ATAC-Seq is performed as a second assay following dilution of droplet contents.

Additional assays for epigenetic profiling can also be performed. In some embodiments, single cell DNA methylation is assayed using single cell bisulfite sequencing (see, e.g., Luo et al, *Science* 357:600-604, 2017; Smallwood et al., *Nature Methods* 11:817-820, 2014; Francis et al, *Cell reports* 10:1386-1397, 2015). In some embodiments, single cells can analyzed by chromatin profiling using ChIP-SEQ. In some embodiments, the epigenetic assay is performed in the double emulsion droplets. In alternative embodiments, the epigenetic assay is performed as a second assay following dilution of droplet contents.

In further embodiments, whole genome sequencing can be performed, e.g., for haplotype analysis or phasing. In some embodiments, the assay is performed in the droplet phase of the method. In alternative embodiments, the assays are performed as a second assay following sorting and dilution of the contents of the droplets. Illustrative whole genome sequencing reactions for single cell genome sequence include multiple displacement amplification (MDA) and Multiple Annealing and Lopping Based Amplification Cycles (MALBAC) (see, e.g., Stepanauskas et al, *Nat. Comm.* 8: Article number 84, 2017; Zong et al, *Science* 338:1622-1626, 2012; Nin et al., Sci Rep 5:11415, 2015; Zhang et al, *Nat. Commun* 6:6822, 2015). In some embodiments, whole genome sequencing is performed in the double emulsion droplets. In alternative embodiments, whole genome sequencing is performed as a second assay following dilution of droplet contents.

In some embodiments a parameter assayed in accordance with the invention is RNA expression using single cell RNA sequencing (RNA-Seq) (see, e.g., Tang et al., *Nat. Methods* 6:377-382, 2009; Ramskolod et al., *Nat. Biotechnology* 30:777-782, 2012; Macosko et al., *Cell* 161: 1202-1214, 2015; WO2016/040476; Klein et al., Cell 161:1187-1201, 2015; WO2016168584; Zheng, et al., *Nature Biotechnology* 34:303-311, 2016; Zheng, et al., *Nat. Commun.* 8: Article number 14049, 2017; WO 2014210353; Zilionis, et al., *Nat Protoc.* 12:44-73, 2017; Cao et al., *Science* 357:661-667, 2017; and Rosenberg et al., 2017, "Scaling single cell transcriptomics through split pool barcoding" bioRxiv preprint Feb. 2, 2017. Both unbiased and targeted approaches may be employed. In some embodiments, the RNA-Seq assay is performed in the double emulsion droplets. In alternative embodiments, RNA-Seq is performed as a second assay following dilution of droplet contents.

In some embodiments, the expression of a protein or panel of proteins can be assessed in individual cells using antibody-based detection methods; or other polypeptides or binding agents that specifically bind to a protein of interest in a cell. Illustrative assays include, but are not limited to, proximity ligation assay and proximity extension assays; immunofluorescence assays and other antibody-based assays. Such an assay can be performed as the first assay or as a second assay. In some embodiments, protein detection methods can be used to identity droplets containing single cells having a desired phenotype which can then be sorted and the single droplets analyzed by another assay, e.g., RNA-Seq. In some embodiments, droplet containing single cells having distinct phenotypes can be pooled for further analysis of the distinct phenotypic populations, e.g., by RNA sequencing or other RNA detection methods.

In some embodiments, the assay performed at the droplet stage is an assay that employs an enzyme such that the volume at the droplet stage provides for a more efficient reaction.

Illustrative First and Second Parameter Analyses of Single Cells:

Expression of One or More Genes of Interest Expression and RNA-Seq

In some embodiments, one parameter that is analyzed is expression of one or more genes of interest to select cells that express that gene ("curated gene expression") and the second parameter is analysis of the complete RNA transcript profile for the selected cells. For example, a droplet-volume reaction can be performed to select cells that express one or more genes of interest, e.g., using an RT-PCR TaqMan® probe assay. Droplets are then sorted based on probe signal and single droplets that are detected by the probe signal are deposited in a compartment for RNA-Seq analysis is performed to evaluate the full expression profile of the individual cells expressing the gene, or genes, of interest. Thus, RNA-Seq analysis of all transcripts is performed only on cells that express one or more genes of interest. Thus, for example, rare cell populations, or cell populations of specific interest, e.g., neural cells or stem cells, can be more fully characterized.

An illustrative curated gene expression-RNA-Seq protocol is as follows:

The following reagents are added for the droplet reaction:
  i. (1) lysis reagents
  ii. (2) TaqMan® probe for a gene(s) of interest (gene sequence, quencher and fluorophore, only emits signal when bound to gene), primers for TaqMan® amplification,
  iii. (3) primers to poly(A) RNA capture (e.g., oligo(dT) 30VN) and RT (template switching oligo),
  iv. (4) RT-PCR enzymes and buffers and
  v. (5) cells with density matching suspensions into the droplet core volume.

Droplets are incubated to allow cells to lyse, the droplets are subjected to thermocycling to perform RT-PCR for the gene(s) of interest using a TaqMan® probe, and RT on the poly(A) transcripts to stabilize the cellular mRNA as cDNA Droplets are sorted by FACS based on the TaqMan® signal to deposit single droplets expressing the gene of interest in 96- or 384-well plates. RNA-Seq is performed in the plates using the plate-volume (and SmartSeq II protocols) per each droplet. The result is a barcoded RNA-Seq single cell library where each cell was specifically selected (using the TaqMan® RT-PCR in the droplet volume and subsequent sorting) to express a gene of interest.

Illustrative reagents, reaction and thermocycling conditions for the curated gene expression protocol are:
  Droplet Core: (1) RT-PCR buffer (50 mM Tris-HCl, pH 8.0, 0.2 mM dNTPs, 75 mM KCl, 9 mM MgCl2, 5 mM DTT, 1M Betaine (optional), 10 U Promega Recombinant RNasin Ribonuclease Inhibitor, 100 U Invitrogen SuperScript II/III RT/Platinum Taq High Fidelity Enzyme Mix), (2) Lysis Buffer (0.01% Digitonin, 0.1% Nonidet P40, 1% Tween-20, 1% BSA), (3) TaqMan® PCR primers and probes for genes of interest (selected) (0.2 uM IDT PrimeTime qPCR probes, custom designed), (4) SmartSeq II RT oligos for PolyA+ mRNA RT (IDT LNA-modified 1 uM TSO, 1 uM Oligo-dT30VN, from Picelli et al., Nature Protocols, 9, 171-181 (2014))
  Droplet Shell: 2.2% Ionic Krytox (FS-H) in HFE 7500 (or similar) fluorinated oil.

Reaction Incubation: Incubate 10 min, room temperature; Reverse transcription (RT): 42-55 C 30-90 min; TaqMan® PCR: 2 min 94 C, 30-50 cycles 15 s 94 C, 30 s 50 C, 1 min 68 C, 5 min 68 C, 15 min 70 C (inactivation).

Illustrative reagents and reaction conditions for the RNA-Seq reaction are:
  Plate Reaction: Reagents and protocols of SmartSeq II (Picelli et al., Nature Protocols, 9, 171-181 (2014)), no substantial changes required
  Reaction Cycling: Similar to Protocols of SmartSeq II (Picelli et al., Nature Protocols, 9, 171-181 (2014)), no substantial changes required.

ATAC-Seq and RNA-Seq

In some embodiments, a method of the present disclosure comprises performing an ATAC-Seq reaction in the single cell droplet and an RNA expression analysis, e.g., RNA-Seq, following sorting of single droplets and dilution of the contents from the broken single droplets. Cells may be labeled for FACs analysis, e.g., using a fluorescent DNA intercalating dye prior to encapsulation in the double emulsion droplet; or may be labeled following encapsulation in the droplet.

In an illustrative embodiment of multi-parameter assay using ATAC-Seq and RNA-Seq analysis, single cells, lysing buffer, a fluorescent DNA intercalating dye to label the cells, and ATAC reagents, including the transposase/dimethyl formamide (DMF), are encapsulated into double emulsion droplets using a microfluidic device that employs separate aqueous streams to introduce the cells and other agents into the droplet. Cells are incubated at 37° C. between 5 and 30 minutes and then maintained at 4° C. throughout the sorting procedure. Following incubation, droplets are sorted by FACS to identify single droplets that contain single cells, which are deposited into individual wells of a multi-well plate. The droplets are conveniently broken by depositing the droplets into dry wells and pausing for 30-60 secs to allow the droplets to pop. The contents of the droplets in each of the individual wells is then diluted, e.g., 10,000- to 100,000-fold, with a buffer comprising reagents for an RNA-Seq analysis using single cell template switching with ribosomal RNA depletion. Barcodes unique for each well containing the processed products from a single cell are added by PCR indexing. The indexed single cell products are then pooled and sequenced by massively parallel sequencing.

Illustrative ATAC and RNA-Seq reagents and buffers in double emulsion droplets are as follows:

ATAC Reaction:
  Droplet Core: (1) Tagmentation Buffer: 1×TD Buffer (10 mM Tris-HCL pH 7.6, 10 mM MgCl2, 10% DMF (optional, chromatin stabilizer), final pH=7.6), (2) Lysis Buffer: 0.1% Nonidet-P40, 0.1% Tween-20, 1% BSA (optional), 0.01% Digitonin, (3) 0.5% PBS containing 200,000-1 M cells/mL during cell loading, (4) Enzyme mix: 50 nM Tn5 transposase in Nextera™ enzyme storage buffer.
  Droplet Shell: 2.2% Ionic Krytox (FS-H) in HFE 7500 (or similar) fluorinated oil.
  Reaction Incubation: 37° C. for 30 minutes, 100 rpm mixing (tagmentation reaction).

RNA-Seq Reaction:
  Plate Reaction: Reagents of SmartSeq II (Picelli et al., Nature Protocols, 9, 171-181 (2014)) with dual-library barcoding using Nextera™ N70X adaptors and combinatorial indexing.

Reaction Cycling: Similar to Protocols of SmartSeq II (Picelli et al., Nature Protocols, 9, 171-181 (2014)) with added tagmentation mosaic sequence and ISPCR dual barcoding per well.

Source of Single Cells

Single cells from any source, including any plant, animal, or microorganism may be analyzed in accordance with the methods of the invention. In some embodiments, cells are eukaryotic cells. In some embodiments, the cells are mammalian cells, e.g., human cells. In some embodiments, the cells are cancer cells, stem cells, neurological cells, peripheral blood mononuclear cells, lymphocytes, e.g., human cancer cells, human stem cells, human neurological cells, human peripheral blood mononuclear cells, or human lymphocytes. In some embodiments, the cells are obtained from a tissue e.g., a human tissue. In some embodiments, the cells are obtained from a tumor, e.g., a human tumor. In some embodiments, cells from transgenically modified organisms may be evaluated, e.g., for screening.

EXAMPLES

The following examples are provided to illustrate, but do not limit, the invention.

FIG. 1, Panels A-C, provide an overview of an illustrative assay of the present disclosure. As shown in Panel A, double emulsion droplets are generated in a microfluidic device, and cells, lysis buffer, and assay reagents are co-encapsulated via separate aqueous streams to generate an aqueous miscible core that is then encased in an immiscible oil shell (~30-50 μm in total diameter, ~10-15 μm in cross-section outer shell diameter, monodispersity in size per sample typically less than 2.5% CV) in a flow-focusing junction with an outer aqueous sheath. Single droplets may be loaded with cells under conditions that produce a desired Poisson distribution (e.g., most droplets contain zero or a single cell. Cells can be lysed within the droplet by the lysis buffer. Depending on the nature of the co-encapsulated assay reagents (e.g., addition of specific DNA or phenotypic dyes), double emulsion droplets subjected to FACS can be analyzed, and gated (or binned) based on cellular presence, lysis efficiency, reaction progress or completion, and/or phenotypic parameters. Panel B illustrates 3-color FACS, for example, one color to evaluate cellular presence, one color as a spectral control, and, optionally a phenotypic parameter. After double emulsion population gates are selected, the population is sorted into multi-well plates or an equivalent, and single droplets with selected characteristics are deposited into wells of one or more multi-well plates (e.g., 96- or 384-well plates) for downstream processing. Generally at least 70% of wells contain a single droplet (≥70% single droplet occupancy is achieved). In Panel C, droplets are broken by osmotic or shear force ("popping" on dry plates) and cellular contents (e.g., nucleic acids) can be extracted and processed. In all assays, plate-based dilution from droplet to plate during single droplet deposition in FACS allows for "one pot" reaction chemistry incompatibilities to be mitigated for multiple biomolecular class purification or library preparation.

FIG. 2, Panels A and B, illustrate a plate-based dilution scheme via single droplet deposition of double emulsion droplets after FACS. In the scheme shown in Panel A, the first library reaction is completed within the droplet volume (~100 pL) and a second library preparation reaction to achieve sequential multi-parameter single cell analysis is completed in the much larger plate volume (e.g. ~10-20 uL) after droplet deposition. This dilution scheme achieves 1,000-100,000-fold dilution, overcoming "one-pot" library preparation and purification issues and incompatibilities. Illustrative multi-parameter single cell analyses possible with double emulsions in the droplet to plate sorting scheme are shown in Panel B.

Figure 3A:
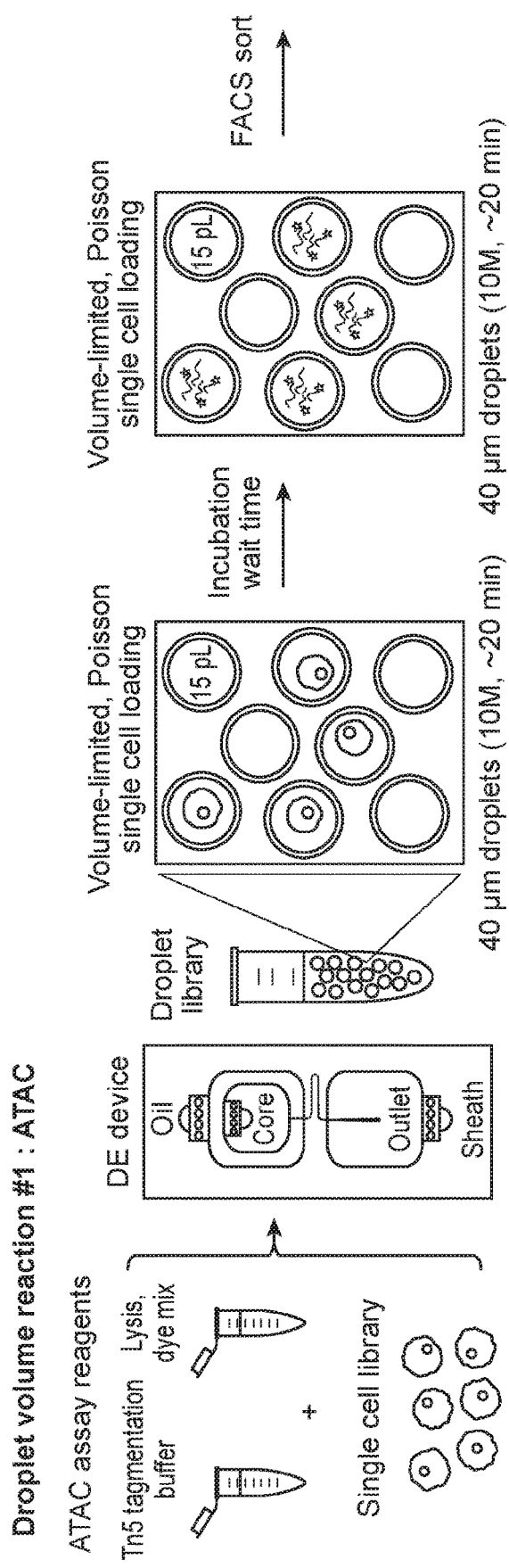
FIG. 3A-C provide an illustrative assay for performing ATAC-Seq and tandem RNA-Seq in the same single cell.
Figure 3B:
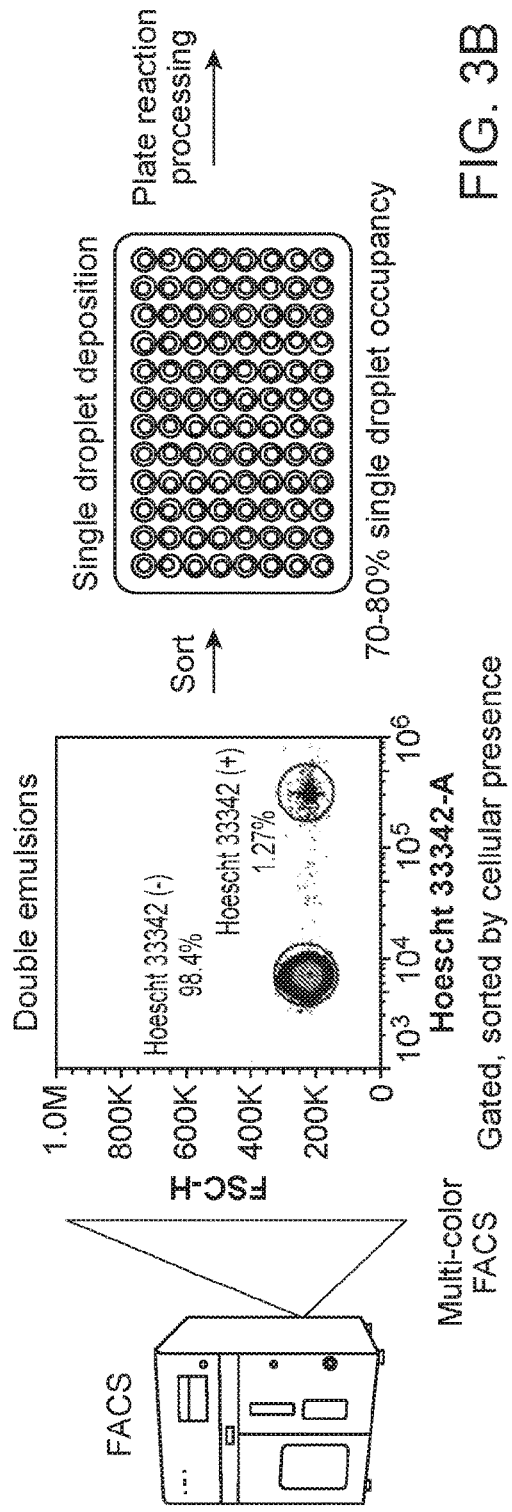
Figure 3C:
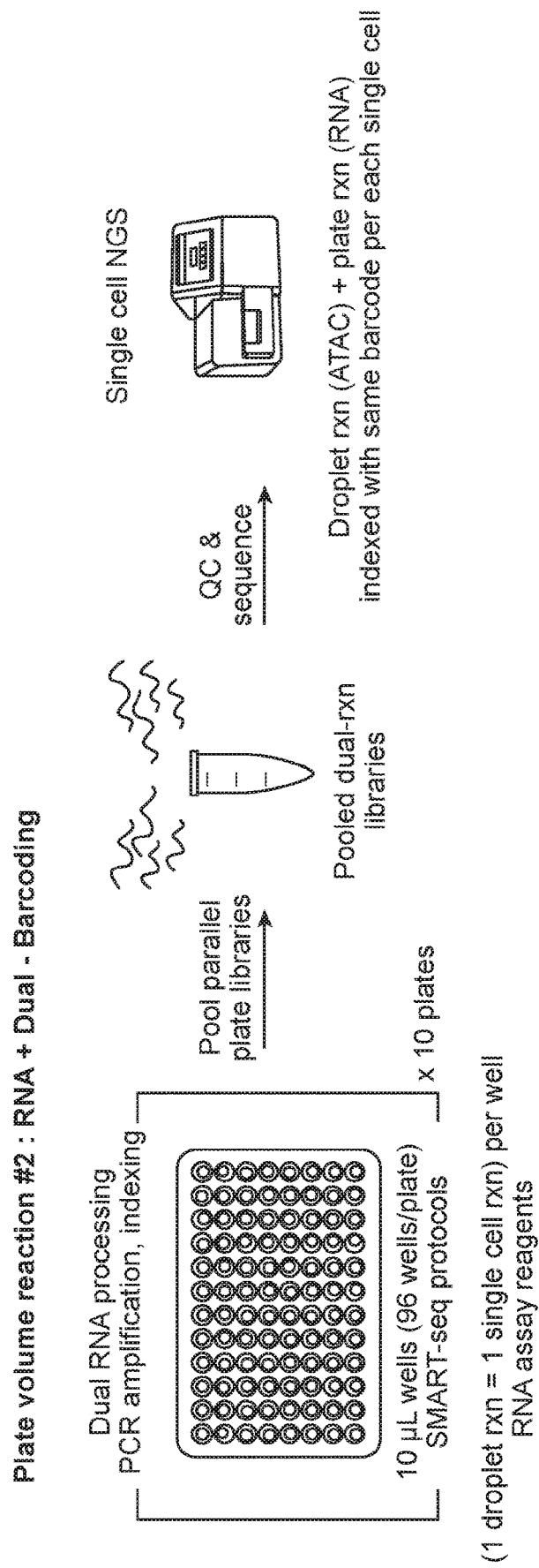

FIG. 3, Panels A-C, provide an illustrative assay for performing ATAC-Seq and tandem RNA-Seq in the same single cell. Panel A depicts an ATAC reaction performed in a droplet volume. Panel B depicts sort of droplets into plates. Panel C depicts an RNA-Seq analysis performed in the plate volume.

Figure 4:
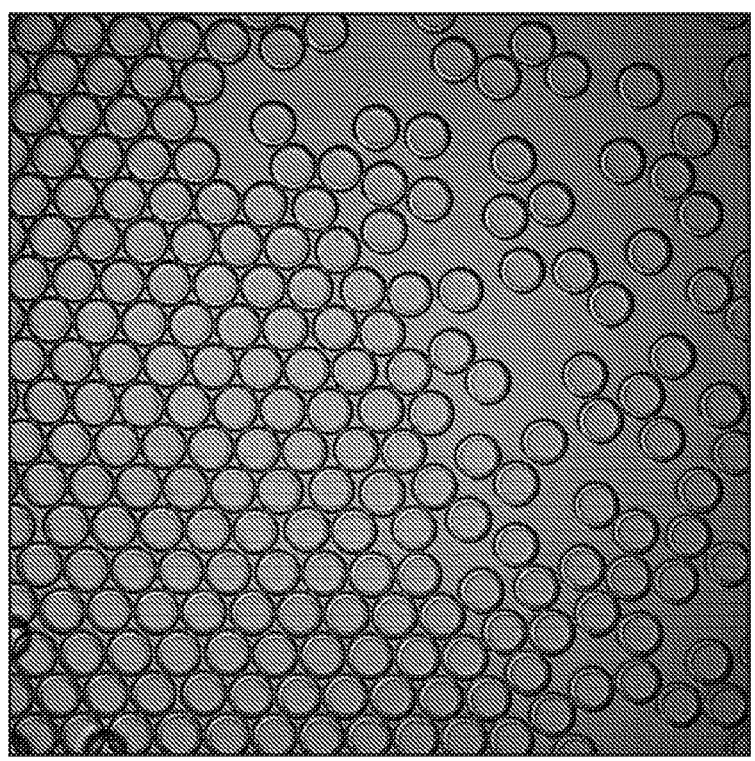
FIG. 4. Optical imaging (brightfield illumination) of representative double emulsions. 60 μm (22-25 μm shell) aqueous/oil/aqueous double emulsions

FIG. 4. Optical imaging (brightfield illumination) of representative double emulsions. Double emulsions have been produced from sizes 20 um to 125 um total diameter.

Figures 5A, 5B:
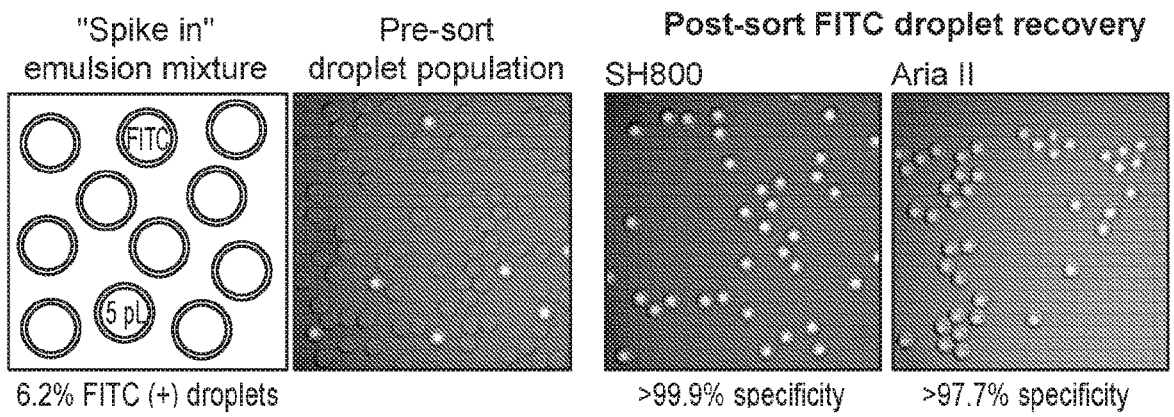
FIG. 5A-D illustrates analysis of droplets via flow cytometry and the ability to restrict sorting to a desired target population of homogenous double emulsions.
Figure 5C:
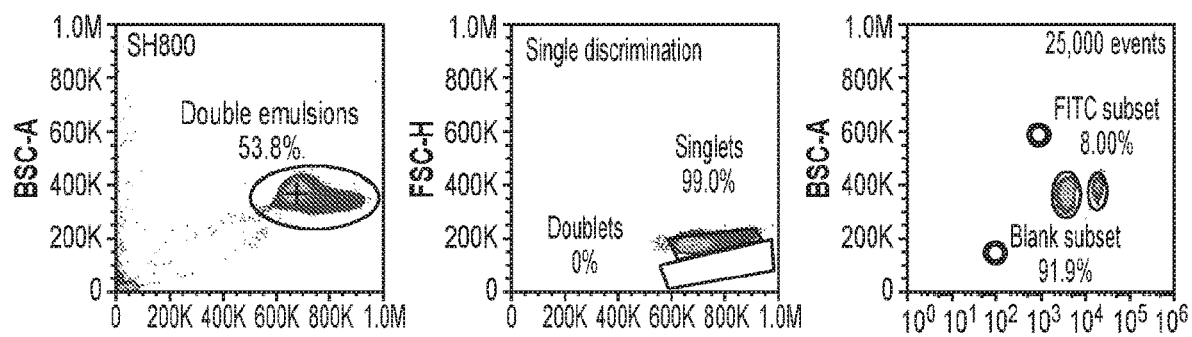
Figure 5D:
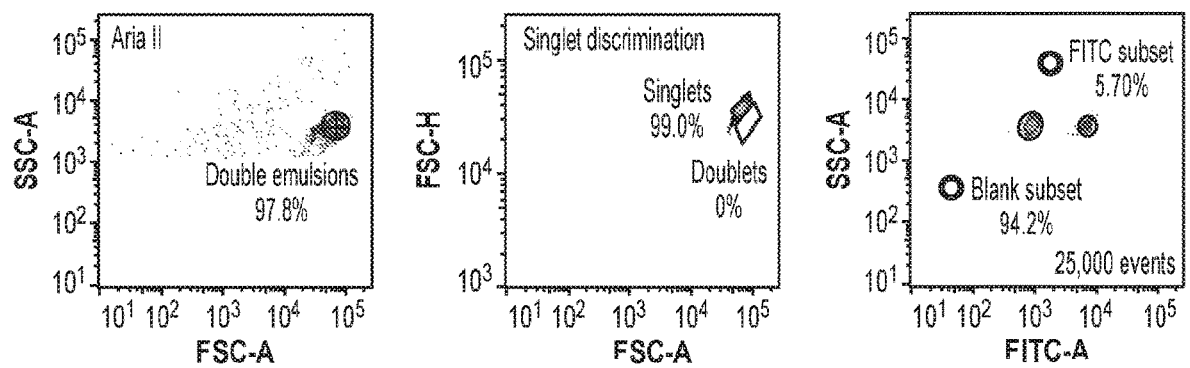

FIG. 5, Panels A-D, illustrate analysis of droplets via flow cytometry and the ability to restrict sorting to a desired target population of homogenous double emulsions. Double emulsions were loaded with FITC-BSA (as the fluorophore) in 1×PBS or 1×PBS alone in the core with a 2% Krytox HFE 7500 fluorinated oil shell, and mixed into a population containing 6.2% FITC-BSA-containing droplets (the "target"). FACS analysis and sorting was performed on a FACSAria™ II (BD Biosciences) sorter with 130 um nozzle and a SH800™ (Sony Biotechnology) with 130 um nozzle. Panel A shows the pre-sort target population. Panel B shows post-sort target (FITC-BSA-containing droplets) enrichment after sort selection for this population in both instruments, with statistics. FACSAria™ II data used a droplet delay modification scheme to select for optimal sort statistics. Panels C and D show FACS ancestry plots from left to right for both sorters, with the final right graphs illustrating concordance with the 6.2% rare population doping rate. FACSAria™ II (Panel D) shows a slightly better dynamic range.

Figure 6D:
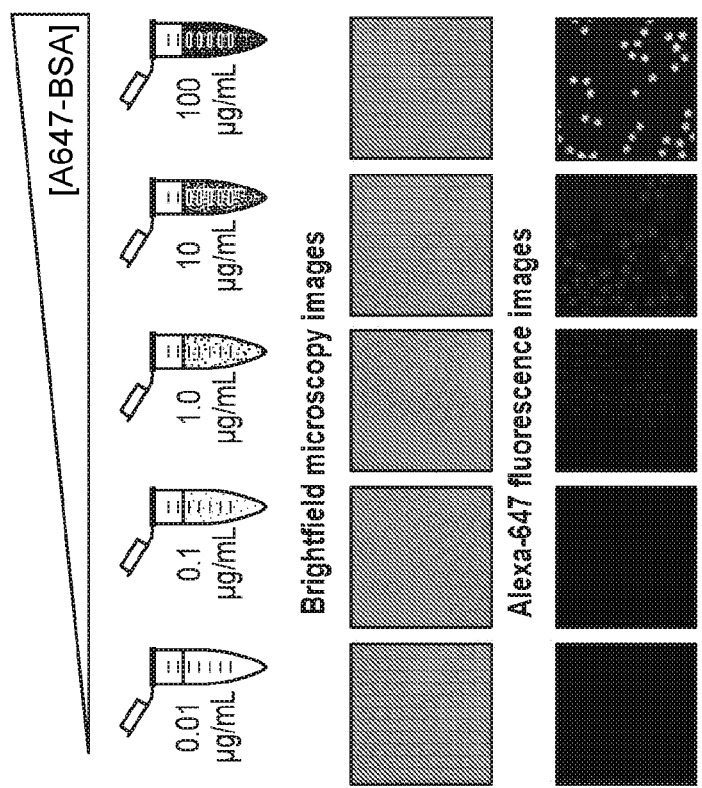
Figure 6E:
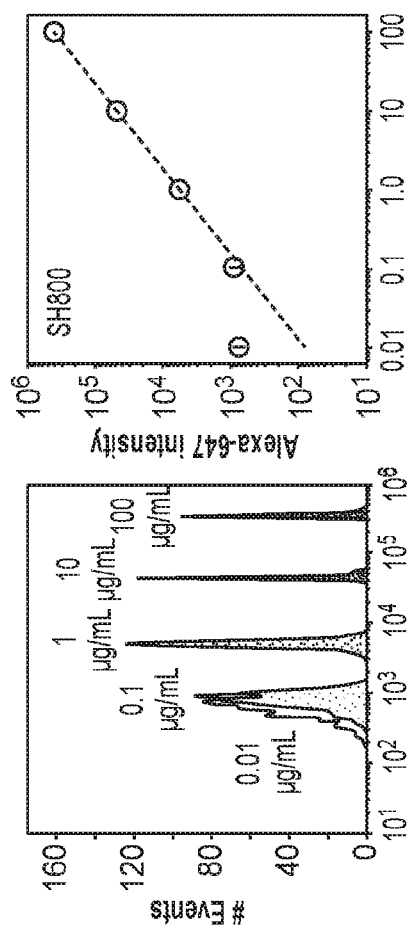
Figure 6F:
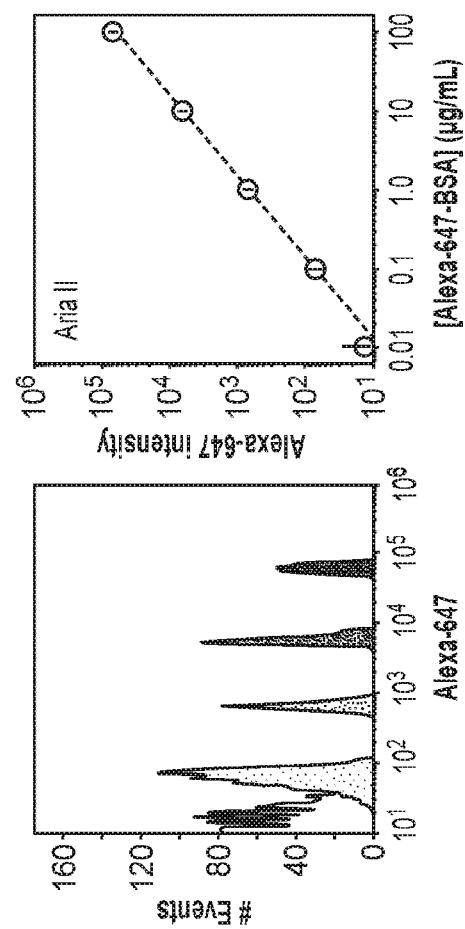

FIG. 6, Panels A-F, show comparative flow dynamic range and sensitivity analysis of 30 um double emulsion droplets containing FITC-BSA as the fluorophore (Panel A) or Alexa-647-BSA (Panel D) as the fluorophore in concentrations ranging from 0.01 ug/mL to 100 ug/mL (5 droplet populations, brightfield and fluorescent channel visualizations shown). Droplets were analyzed on the FACSAria™ II (BD Biosciences) (Panels C and F) and SH800 Cell Sorter (Sony Biotechnology) (Panels B and E) for each dye. Peaks for each dye concentration are extremely well-seperated using the droplet formulations as indicated for all populations to 0.1 ug/mL for both sorters, with better lower range sensitivity and discrimination observed by the FACSAria™ II past 1 ug/mL. Typical cell staining dyes are of equivalent photon counts to FITC-BSA within the 1 ug/mL range. Comparative flow micrographs of blank, 1 ng/mL (1:1000) and 100 pg/mL (1:10,000) FITC-loaded 30 um double emulsions on FACSAria™ II (BD Biosciences) (top) and SH800 Cell Sorter (Sony Biotechnology) (bottom). First two panels from 1:1000 FITC loading data to show scatter profiles. This figure demonstrates dye discrimination in the right-most last panel of three droplet population across two instruments.

Table 1 shows optimized double emulsion sorting parameters for FACS and single droplet deposition on Aria II (BD) and SH800 (Sony) sorters.

| Parameters | Aria II (BD Biosciences) | SH800 (Sony) |
| --- | --- | --- |
| FSC | 25 | 1 |
| Threshold | 1200 | 0.6% gain |
| SSC (or BSC) | 170 | 28% gain |
| APC | 500 | 40% |
| FITC | 525 | 40% |
| DAPI | 455 | 33% |
| Analysis Mode | Log FSC vs. SSC | Linear BSC vs. SSC |
| Trigger | FSC | FSC |
| Sample Pressure or Flow Rate | 3 (Flow Rate) | 9 psi |
| Agitation | 300 rpm | High |
| Nozzle or Chip Size | 130 μm | 130 μm |
| Frequency | 14.5 kHz | 12 kHz |
| System Pressure | 10 psi | 9 psi |

FIG. 7, Panels A-C. Panel A shows brightfield images of optical 96-well plate sorting on SH800 (Sony) from a dilutional series down to single droplet resolution for single droplet deposition. Sorting has been successfully performed on both 96- and 384-well plates. Panel B shows 96-well plate statistics for a representative plate (counts, sample std dev.) with well-based technical replicates for both platforms demonstrating that 70% single droplet deposition efficiency can be obtained. Panel C provides a table showing data that accompanies Panel B for a representative plate sort for both platforms.

FIG. 8, Panels A-C, show nucleic acid recovery and quantitative PCR (qPCR) for a small (175 bp DNA fragment) from single droplet deposition and droplet lysis in plates. Panel A shows droplet deposition plate map and assay schematic indicating uniform loading of ~3M DNA fragments per droplet. Droplets (100, 10, or 1) were deposited in wells of a 96-well plate as indicated. Wells containing no droplets are noted as NTC (no template control). Panel B shows qPCR results (10 uL reactions). Raw qPCR pickup curves (left) showed discrimination between 1 drop set point wells and NTC wells (lightest color, right shifted cycles). The 1 drop set point wells clustering with NTC likely have 0 droplets deposited, in good concordance with optical plate counting data (FIG. 7A-C). The results showed tight single droplet cluster with >60% of observations at single-droplet Ct values (standard curve not shown) (leftmost cluster), also consistent with plate statistics data. The middle inset graph shows Cq values for 1, 10, 100 droplet set point wells, with excellent clustering and good discrimination (bimodal single droplet set point data reflects 0 or 1 single droplet occupancy as noted). The right-most inset graphs shows observed vs expected for 1 and 10 droplets set point wells (spread in 10 droplet set point wells reflects 60-70% well occupancy statistics). Panel C shows raw qPCR curves for Sony and Aria sorters for the same test. Note that NTC pickup in the lightest grey reflects presence of primer dimers (to visualize empty well clustering), as determined by melt curve analysis.

FIG. 9 shows single cell loading in double emulsion droplets. Panel A shows an exemplary assay where double emulsions droplets of 40 um in diameter (15 pL core volume) are loaded with single cells of interest and assay reagents, including cell staining dyes (Hoescht 33342 and PI) as well as lysis reagents (0.1% NP-40, 1% Tween-20, 0.1% Digitonin). Panel B shows exemplary loading images of planarian worm single cells in droplets with Hoechst (dark purple) and PI (red) visualization (demonstrating cell lysis). Panels C, D, and E show FACS analysis of double emulsion droplets (Panel C) with discrimination by cell presence (Panel D) and cell lysis (Panel E, PI presence). Cell loading statistics are maximized without active concentration (e.g., inertial loading) at ~1-5%, if the initial cell concentration is 1-5M cells/mL respectively, because of the small volume of the double emulsion droplet core. Double emulsions can be produced rapidly (10M in less than 20 min) so large cellular populations can be analyzed even with low cell occupancy statistics.

Figure 10A:
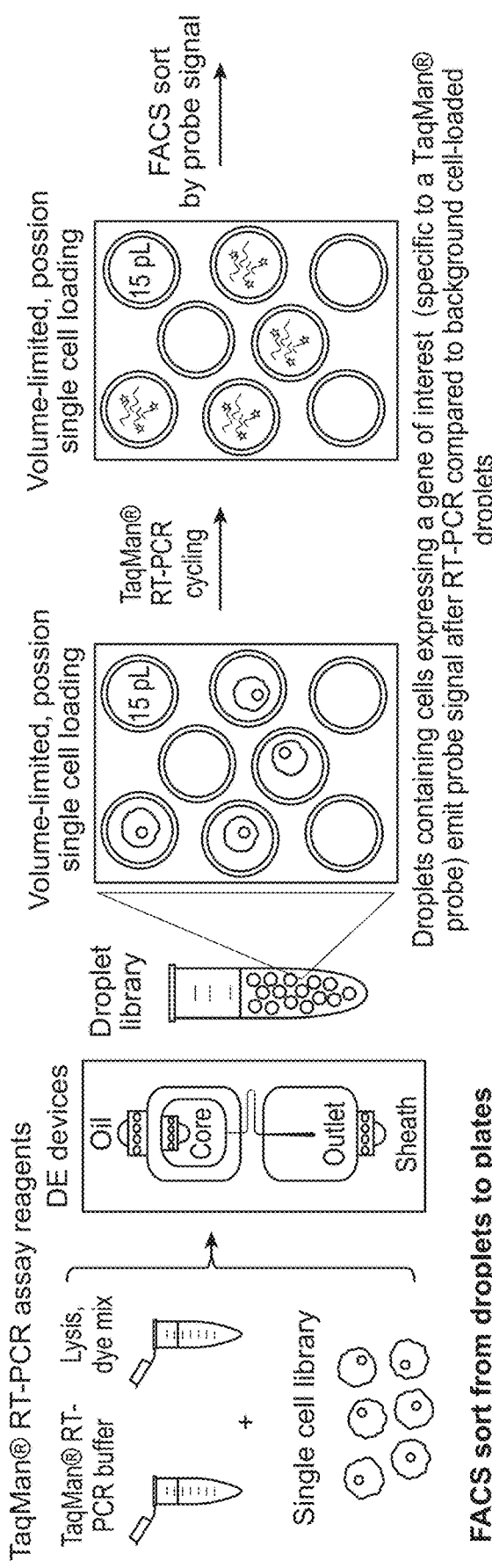
FIG. 10A-C, provide an illustrative assay for performing curated gene expression profiling of cells for one or more genes of interest using a TaqMan® probe RT-PCR assay, sorting to select for a subpopulation of cells expressing the gene of interest, and tandem RNA-Seq in the same single cell.
Figure 10B:
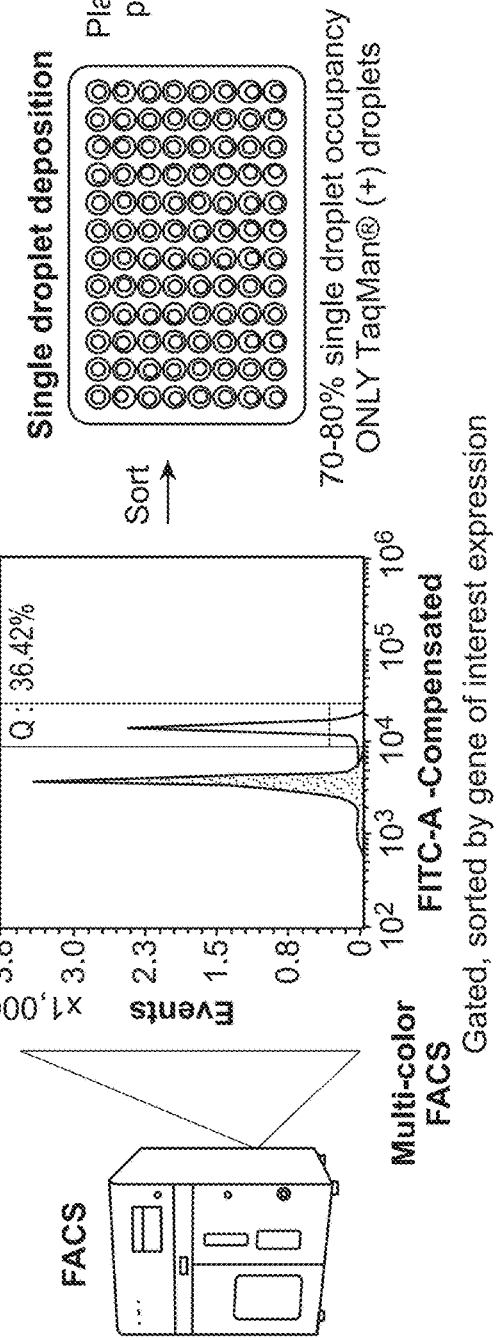
Figure 10C:
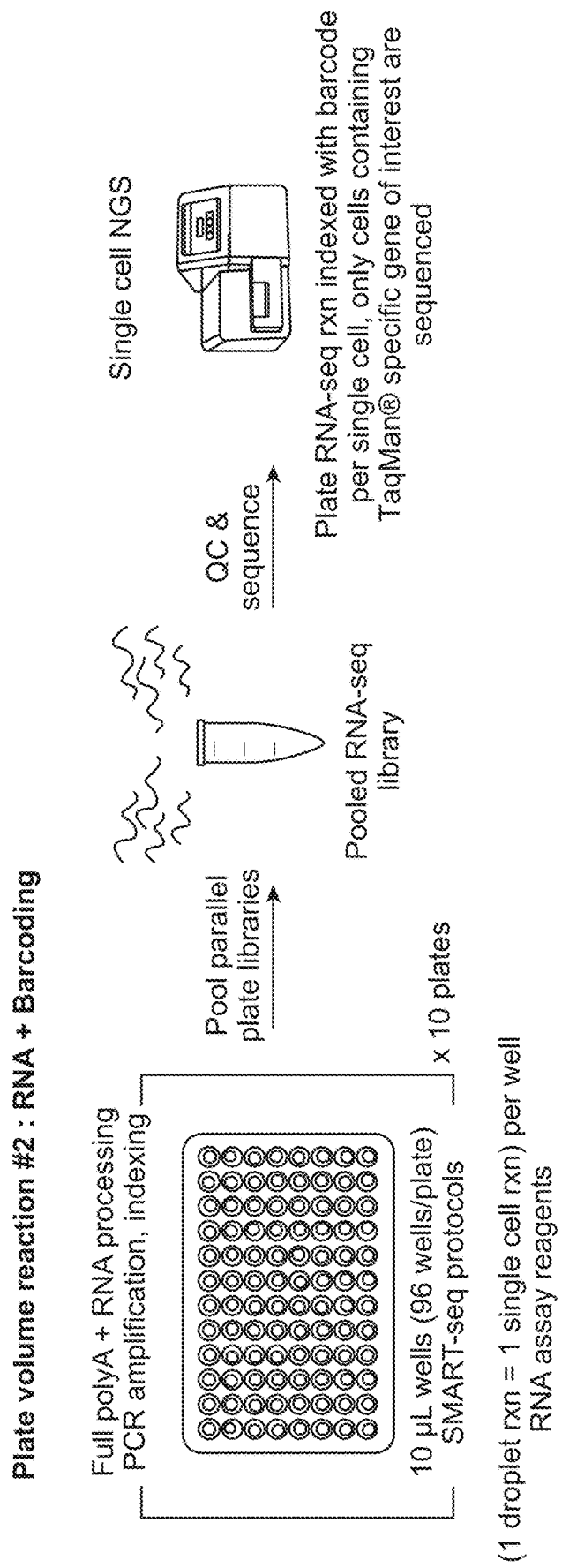

FIG. 10, Panels A-C, provide an illustrative assay for performing curated gene expression profiling in one or more genes of interest using TaqMan® PCR and tandem RNA-Seq in the same single cell. Panel A depicts a droplet-volume reaction and section of cells expressing a gene of interest by TaqMan® RT-PCR. Panel B shows selection for droplets containing GAPDH (FITC+, selected cluster) using a FITC-based TaqMan® probe after RT-PCR before sorting of single droplets. Panel C shows a plate volume RNA-Seq reaction.

In the assay shown FIG. 10, the droplet-volume reaction selects for cells expressing a gene of interest by using a TaqMan® probe for the cDNA of that gene of interest and then, downstream in the plate volume, full RNA-seq for all transcripts (unbiased, Poly(A)+ approach, SmartSeq II protocols) is performed. Thus, RNA-Seq analysis of all transcripts is performed only on cells that express a gene marker of interest.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference with respect to the material for which they are expressly cited.

What is claimed is:

1. A method of producing a library of single cells for multi-parameter analysis, comprising:
   (a) generating a population of double emulsion droplets at least some of which comprise single cells encapsulated therein, wherein the double emulsion droplets further comprise reagents for a first single cell assay to analyze a first parameter;
   (b) incubating the droplets for a time sufficient to generate a reaction product for the first single cell assay;
   (c) sorting the population of droplets by flow cytometry to select for single droplets comprising one or more cells, or the contents of one or more cells;
   (d) distributing single droplets that comprise single cells into separate dry compartments;
   (e) breaking individual droplets in each separate dry compartment by shear or osmotic force to produce a plurality of individual compartments each with the content of a single droplet;
   (f) diluting the contents of individual compartments by at least 500-fold to provide a diluted reaction volume; and
   (g) measuring a second parameter in a second single cell assay in the diluted reaction volume.

2. The method of claim 1, further comprising a step of processing the contents of the diluted reaction volume for analysis of the reaction product for the first single cell assay.

3. The method of claim 1, wherein Step (f) employs a diluent that comprises reagents that differ from the first single cell assay reagents.

4. The method of claim 1, wherein the droplets of Step (a) comprise cell-lysing buffer.

5. The method of claim 1, wherein Step (f) comprises diluting the contents by 1,000-fold to 100,000-fold.

6. The method of claim 1, wherein Step (c) comprises sorting based on DNA content.

7. The method of claim 6, wherein at least some of the droplets selected in Step (c) contain haploid cells, or the contents of said haploid cells; at least some of the droplets selected in Step (c) contain diploid cells or the contents of said diploid cells; or at least some of the droplets selected in Step (c) contain cells having a ploidy greater than diploid, or the content of said cells having a ploidy greater than diploid.

8. The method of claim 1, wherein the cells are labeled with a fluorescent DNA intercalating dye for sorting by flow cytometry; the cells are labeled with a fluorescent assay reagent for sorting by flow cytometry; or the cells are labeled with a fluorescent dye coupled to a protein for sorting by flow cytometry, optionally where the protein is an antibody.

9. The method of claim 1, wherein the reaction product generated in Step (b) is not fluorescently labeled; the reaction product generated in Step (b) is not detectably labeled; and/or the presence, absence or amount of the reaction product generated in Step (b) is not a basis for sorting droplets in Step (c).

10. The method of claim 1, wherein the first single cell assay and second single cell assay are selected from the group consisting of the following:
the first single cell assay is ATAC-Seq and the second single cell assay is an RNA analysis assay, optionally RNA-Seq; whole genome sequencing; or a protein detection assay; or
the first single cell assay is a protein detection assay and the second single cell assay is RNA-Seq; ATAC-Seq, or whole genome sequencing;
or the first single cell assay detects expression of at least one gene of interest and the second single cell assay is an RNA-Seq assay.

11. The method of claim 1, wherein the first single cell assay detects expression of at least one gene of interest and the second single cell assay is an RNA-Seq assay and:
the first single cell assay comprises an RT-PCR amplification reaction to specifically detect expression of the least one gene of interest, wherein the RT-PCR reaction comprises an oligonucleotide labeled with a detectable label, and wherein the oligonucleotide specifically hybridizes to a target nucleic acid sequence in the gene of interest; and
the sorting Step (c) comprises selecting droplets that contain a signal from the detectable label.

12. The method of claim 1, wherein the double emulsion droplet is about 20-125 micrometers in diameter.

13. The method of claim 2, wherein the processing step comprises an amplification reaction to index the contents of the compartments by the addition of barcodes unique to each compartment; and pooling the contents of the individual compartments for further analysis, optionally wherein the pooled contents are sequenced by massively parallel sequencing.

14. The method of claim 1, wherein the compartments are components of a multi-well plate, optionally where the multi-well plate comprises 96, 384, or 1536 wells.

15. The method of claim 1, wherein greater than 50% of the compartments contain content from a single cell; or greater than 80% of the compartments contain content from a single cell.

16. The method of claim 1, wherein the single cells of (a) are eukaryotic cells.

17. The method of claim 16, wherein the eukaryotic cells are mammalian cells.

18. The method of claim 17, wherein the mammalian cells are human cells.

19. The method of claim 17, wherein the cells are tumor cells, embryonic stem cells, neural cells, or lymphocytes.

20. The method of claim 1, wherein Step (c) comprises selecting for droplets in which a reaction occurred.

* * * * *

UNITED STATES PATENT AND TRADEMARK OFFICE
CERTIFICATE OF CORRECTION

| | | |
|---|---|---|
| PATENT NO. | : 12,227,741 B2 | Page 1 of 1 |
| APPLICATION NO. | : 17/257509 | |
| DATED | : February 18, 2025 | |
| INVENTOR(S) | : Polly Fordyce et al. | |

It is certified that error appears in the above-identified patent and that said Letters Patent is hereby corrected as shown below:

In the Specification

In Column 1, Line 4, Insert:
-- FEDERALLY SPONSORED RESEARCH AND DEVELOPMENT
This invention was made with Government support under contract GM123641 awarded by the National Institutes of Health. The Government has certain rights in the invention. --.

Signed and Sealed this
Sixth Day of May, 2025

Coke Morgan Stewart
*Acting Director of the United States Patent and Trademark Office*